US005693507A

United States Patent [19]
Daniell et al.

[11] Patent Number: 5,693,507
[45] Date of Patent: Dec. 2, 1997

[54] GENETIC ENGINEERING OF PLANT CHLOROPLASTS

[75] Inventors: Henry Daniell, Moscow, Id.; Bruce A. McFadden, Pullman, Wash.

[73] Assignee: Auburn University, Auburn University, Ala.

[21] Appl. No.: 278,555

[22] Filed: Jul. 20, 1994

Related U.S. Application Data

[63] Continuation of Ser. No. 985,451, Dec. 3, 1992, abandoned, which is a continuation of Ser. No. 638,565, Jan. 7, 1991, abandoned, which is a continuation-in-part of Ser. No. 249,616, Sep. 26, 1988, abandoned.

[51] Int. Cl.$^6$ ............................ C12N 15/82; C12N 5/04; C12N 15/29; A01H 5/00
[52] U.S. Cl. ............................ 435/172.3; 435/240.4; 435/320.1; 435/69.1; 800/205; 800/DIG. 58; 536/23.2; 536/23.6; 536/24.1
[58] Field of Search ............................ 800/205, DIG. 58; 435/172.3, 240.4, 320.1, 69.1; 536/23.2, 23.6, 24.1

[56] References Cited

FOREIGN PATENT DOCUMENTS 2183660  6/1987  United Kingdom ............... 435/172.3

OTHER PUBLICATIONS

DeBlock et al. 1985. EMBO J. 4: 1367–1372.
Bradley et al. 1985. EMBO J. 4: 3641–3648.
Overbeeke et al. 1984. Plant Mol. Biol. 3:235–241.
Overbeeke et al. 1984. pp. 461–468. In: Innovations in Biotechnology, Houwink et al., eds., Elsevier: Amsterdam.
Klein et al. 1987. Nature 327: 70–73.
"Optiminzation of delivery of foreign DNA into hight–plant chloroplasts" Guang–Ning Ye, et al., in *Plant Molecular Biology*, vol. 15: 809–819 (1990).
"Stable transformation of plastids in higher plants" by Svab et al., in *Proceedings of the Natl. Acad. Sci.*, vol. 87: 8526–8530 (1990).
"Transient foreign gene expression in chloroplasts of cultured tobacco cells after bolistic delivery of chloroplast vectors" by H. Daniell et al. in the *Proceedings of the Natl. Acad. Sci.* vol. 87: 88–92 (1990).
"Uptake and expression of bacterial and cyanobacterial genes by isolated"Stable cucumber etioplasts by H. Daniell and B.A. McFadden, in *Proceedings of the Natl. Acad. Sci.*, vol. 84: 6349–6353 (1987).
"Mitochondrial Transformation in Yeast by Bombardment with Microprojectiles" by Stephen A. Johnston, et al., in *Science*, vol. 240: 1538–1541 (1988).
"Chloroplast Transformation in *chlamydomonas* with High Velocity Microprojectiles" by John E. Boynton, et al., in *Science*, vol. 240: 1534–1537 (1988).
"Studies on *chlamydomonas* Chloroplast Transformation: Foreign DNA Can Be Stably Maintained in the Chromosome" by Alan D. Blowers, et al., in The Plant Cell, vol. 1: 123–132 (1989).
"Interspecific chloroplast recombination in a *nicotiana* somatic hybrid" by Peter Medgyesy, et al., in *Proc. Natl. Acad. Sci. USA*, vol. 82: 6960–6964 (1985).
"Localization of Replication Origins in Pea Chloroplast DNA" by R. Meeker et al., in *Molecular and Cellular Biology*, vol. 8: 1216–1223 (1988).
"Leading organellar proteins along new pathways: the relocation of mitochondrial and chloroplast genes to the nucleus" by Phillip Nagley and Rodney J. Devenish, in *TIBS*, vol. 14: 31–35 (1989).
"Chloroplast promoters" by Handley–Bowden and Chua, in *Trends and Biochemical Sciences*, vol. 12: 67–70 (1987).
"Isolated cell organelles and subprotoplasts: their roles and somatic cell genetics" by H. Lorz in *Plant Genetic Engineering*, Chapter 4: 27–57 (1984).

*Primary Examiner*—David T. Fox
*Assistant Examiner*—Elizabeth C. Kemmerer
*Attorney, Agent, or Firm*—Weiser & Associates, P.C.

[57] ABSTRACT

Novel chimeric constructions and methods for their use are provided for expression of exogenous genes in a plant chloroplast. Particularly, expression is achieved by the use of a chloroplast or bacterial 5' untranslated region in the expression cassette. The expression cassette may be integrated into the chloroplast genome by the use of chloroplast DNA flanking sequences, or may replicate autonomously if provided with a chloroplast origin of replication. Plants and cells containing the transformed chloroplasts are also provided. The constructs may be used with both monocotyledenous and dicotyledenous chloroplasts.

37 Claims, 15 Drawing Sheets

1

GENETIC ENGINEERING OF PLANT CHLOROPLASTS

CROSS-REFERENCE TO RELATED APPLICATIONS

This is a continuation of application Ser. No. 07/985,451, filed Dec. 3, 1992, now abandoned; which is a continuation of application Ser. No. 07/638,565, filed Jan. 7, 1991, now abandoned; which is a continuation in part of U.S. patent application Ser. No. 249,616 filed Sep. 26, 1988, now abandoned, which disclosures are hereby incorporated by reference.

INTRODUCTION

1. Technical Field

This invention relates to methods and compositions for transformation of plant chloroplasts as well as the resulting cells and plants containing transformed chloroplasts.

2. Background

Many techniques have been proposed for the transfer of DNA to plants such as direct DNA uptake, microinjection of pure DNA and the use of viral or plasmid vectors. The strategies for gene transfer involve the introduction of foreign DNA into cells or protoplasts followed by integration into the nuclear genome. However, eukaryotic cells, more particularly plant cells, contain distinct subcellular compartments or organelles delimited by characteristic membrane systems which perform specialized functions within the cell.

In photosynthetic leaf cells of higher plants the most conspicuous organelles are the chloroplasts, which exist in a semi-autonomous fashion within the cell, containing their own genetic system and protein synthesis machinery, but relying upon a close cooperation with the nucleo-cytoplasmic system in their development and biosynthetic activities. The chloroplast present in leaf cells is one developmental stage of this organelle. Proplastids, etioplasts, amyloplasts, and chromoplasts are different stages. The embodiments of this invention apply to the organelle "at large" which will be referred to as a "chloroplast".

The most essential function of chloroplasts is the performance of the light-driven reactions of photosynthesis including fixation of carbon dioxide. However, chloroplasts carry out many other biosynthetic processes of importance to the plant cell, such as synthesis of fatty acids. In addition, the reducing power of light-activated electrons drives the reduction of nitrites ($NO_2^-$) to ammonia ($NH_3$) in the chloroplast; this ammonia provides the plant with nitrogen required for the synthesis of amino acids compartmentalized in the chloroplast and nucleotides.

Other functions in which the chloroplast is involved are of interest to the agriculture industry. For example, many herbicides act by blocking functions which are performed within the chloroplast. Triazine derived herbicides inhibit photosynthesis by displacing a plastoquinone molecule from its binding site in the 32 kDa polypeptide of photo system II. This 32 kDa polypeptide is encoded by the chloroplast genome and synthesized in the organelle. Mutant plants resistant to triazine herbicides have been obtained; they contain a mutant 32 kDa protein in which the plastoquinone can no longer be displaced by triazine herbicides.

Other herbicides are known to block specific steps in amino acid synthesis. For example the sulfonylureas are known to inhibit acetolactate synthase which is involved in isoleucine and valine synthesis. Glyphosate inhibits the function of 5-enol-pyruvyl-3-phosphoshikimate synthase, an enzyme involved in the synthesis of aromatic amino acids. These enzymes are nuclear encoded but are translocated as precursors into the chloroplast.

Synthesis and import into the chloroplast of precursor proteins are highly energy consuming processes. It would therefore be of interest to engineer foreign genes, particularly those which have products which are functional within a chloroplast, through the chloroplast genome instead of the nuclear genome. By chloroplast is intended both mature and immature forms as well as organelles having substantially similar function in tissues other than leaf.

Relevant Literature

Uptake and expression of bacterial and cyanobacterial genes by isolated cucumber etioplasts (immature chloroplasts) has been described. Daniell and McFadden, *Proc. Nat'l Acad. Sci. (USA)* (1987) 84: 6349–6353. Stable transformation of chloroplasts of *Chlamydomonas reinhardtii* (a green alga) using bombardment of recipient cells with high-velocity tungsten microprojectiles coated with foreign DNA has been described. See, for example, Boynton, et al. *Science* (1988) 240: 1534–1538; Blowers, et al. *Plant Cell* (1989) 1: 123–132 and Debuchy et al., *EMBO J.* (1989) 8: 2803–2809. The transformation technique, using tungsten microprojectiles, is described by Kline et al. *Nature* (London)(*1987*) 327: 70–73. Manipulation of chloroplast genes has been described, for example, generation of chloroplast mutants, Maliga et al., *Nature* (1975) 255: 401–402; protoplast fusion, Belliard et al., *Mol. Gen. Genet* (1978) 165: 231–237; organelle inactivation, Aviv et al., *Plant Cell Rep.* (1986) 3: 227–230; and chloroplast recombination, Medgyesy et al., *Proc. Nat'l Acad. Sci. USA* (1985) 82: 6960–6964.

Tewari and coworkers have recently mapped two replication origins in pea cpDNA by electron microscopic analysis. Both of the origins of replication, identified as displacement loops (D loops), were found to be highly active in DNA synthesis when used as templates in a partially purified replication system from pea chloroplasts (Cheung et al., supra, Merker et al., *Mol. Cell. Biol.* (1985) 8: 1216–1223 and Boutry et al. *Nature* (London) (1987) 328: 340–342).

Methods for targeting foreign gene products into chloroplasts (Shrier et al., *EMBO J.* (1985) 4: 25–32) or mitochonbria (Boutry et al., supra) have been described. See also Tomai et al. *Gen. Biol. Chem.* (1988) 263: 15104–15109 and U.S. Pat. No. 4,940,835 for the use of transit peptides for translocating nuclear gene products into the chloroplast. Methods for directing the transport of proteins to the chloroplast are reviewed in Kenauf *TIBTECH* (1987) 5: 40–47. Articles relating to herbicide tolerance and resistance include Shah et al. *Science* (1986) 233: 478–481 and Mazur et al *World Biotech* (1985) 2: 97–108.

SUMMARY OF THE INVENTION

In accordance with the subject invention, methods and compositions are provided for introducing heterologous DNA into the chloroplast genome. The method includes the steps of preparing an expression cassette which includes a DNA fragment comprising a sufficient portion of the 5' untranslated region of a bacterial or a chloroplast gene to provide for transcription and translation of the gene of interest, the gene of interest and a translational and transcriptional termination region functional in the chloroplast. The expression cassette may optionally include DNA sequences which provide for integration of the gene of interest into the chloroplast genome, and/or an origin of replication capable of providing for replication of a gene of interest in the chloroplast. Preferred techniques for obtaining transformation of the expression cassette into the chloroplast include bombardment of chloroplast containing cells or tissue with high density metallic particles to which the expression cassette has been absorbed. The method finds use in obtaining cells containing transgenic chloroplasts, including both dicotylenous and monocotylenous cells.

DETAILED DESCRIPTION OF THE SPECIFIC EMBODIMENTS

Figure 1:
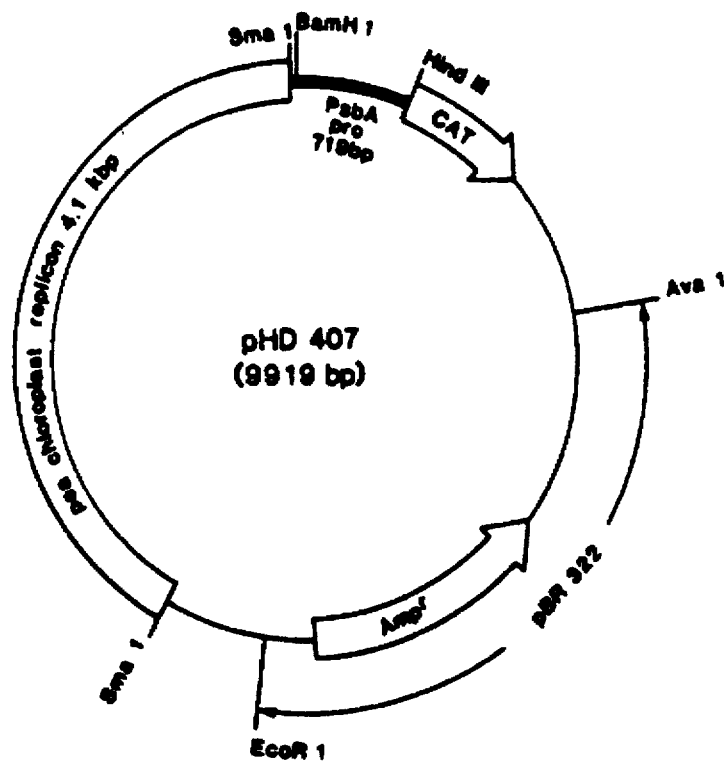
FIG. 1 shows the plasmid pHD407 which carries a 4.1-kbp SmaI fragment insertion containing the origin of replication (D loop) from pea cpDNA inserted into pHD312. The plasmid pHD312 contains the entire promoter and 5' untranslated region of the pea psbA gene inserted 5' proximal to the promoterless cat gene present in the promoter selection vector pkk232-8.

Methods and compositions are provided for obtaining cells containing chloroplasts into which heterologous DNA has been inserted. The method includes the steps of preparing an expression cassette. By expression cassette is intended a DNA construct comprising a coding sequence and appropriate control sequences to provide for proper expression of the coding sequence in the chloroplast. The expression cassette generally includes the following minimum components, the 5' untranslated region from a microorganism gene or chloroplast gene such as psbA which will provide for transcription and translation of a DNA sequence encoding a polypeptide of interest in the chloroplast; a DNA sequence encoding a polypeptide of interest such as genes which provide for herbicide resistance or encode insecticidal proteins; and a translational and transcriptional termination region such as a 2' inverted repeat region of a chloroplast gene that could stabilize RNA of introduced genes, thereby enhancing foreign gene expression. A host cell which contains chloroplasts is transformed with the expression cassette and then the resulting cell containing the transformed chloroplasts is grown to express the polypeptide of interest. The cassette may optionally include an antibiotic resistance gene in addition to a mutated native chloroplast gene such as rbcL or 16 SrRNA. In this option, expression of a desirable alteration of a native protein may be favored in transformed chloroplasts by antibiotic selective pressure.

Typically, the expression cassette is flanked by convenient restriction sites for insertion into an appropriate genome. The expression cassette may be flanked by DNA sequences obtainable from chloroplast DNA which facilitate stable integration of the expression cassette into the chloroplast genome, particularly by homologous recombination. Alternatively, the expression cassette may remain unintegrated by including an origin of replication such as is obtainable from chloroplasts which is capable of providing for replication of the heterologous DNA in the chloroplast.

Plants containing these cells can be generated and grown to produce seed. The system finds use in the production of cells and plants wherein polypeptides of interest can be expressed directly in the chloroplast, for example, to provide for herbicide resistance.

Transformation of the chloroplast genome as opposed to the nuclear genome has several advantages. For example, chloroplast genes in general are maternally inherited. It therefore may be safer to release chloroplast transgenic plants into the environment since the possibility of "escapes" of foreign genes through dispersal of pollen grains is eliminated. Further, it is possible to introduce multiple copies of foreign genes into the chloroplast genome as opposed to the limited number of functional copies of a foreign gene which typically may be introduced via the nuclear genome. Plants engineered through the chloroplast genome rather than the nuclear genome also could have a significant energy advantage since synthesis and import of precursor proteins into a cell organelle are highly energy consuming and rate limiting processes.

In preparing the expression cassette, the various DNA sequences may normally be inserted or substituted into a bacterial plasmid. Any convenient plasmid may be employed, which will be characterized by having a bacterial replication system, a marker which allows for selection of the bacterium, and generally one or more unique, conveniently located restriction sites. The plasmids, or vectors, may include such vectors as pUC, pBR322, pBlueScript, and pGEM, the particular plasmid being chosen based on the nature of the markers, availability of convenient restriction sites, copy number and the like.

A strategy which allows for the stepwise combination of the different fragments is then defined. As necessary, the fragments may be modified by employing synthetic adapters, adding linkers, employing in vitro mutagenesis or primer repair to introduce specific changes in the sequence, which may allow for the introduction of a desired restriction site or a suitably altered biological activity for removing superfluous base pairs or the like. By appropriate strategies, the number of manipulations required as well as the degree of selection required at each stage of manipulation can be minimized. After each manipulation, the vector containing the manipulated DNA can be cloned, the clones containing the desired sequences isolated, and the vector isolated and purified. As appropriate, hybridization, restriction mapping or sequencing may be employed at each stage to insure the integrity and correctness of the sequence.

For transcription and translation of the DNA sequence encoding a polypeptide of interest, the entire promoter region from a gene capable of expression in the chloroplast generally is used. The promoter region may include promoters obtainable from chloroplast genes, such as the psbA gene from spinach or pea, the rbcL and atpB promoter region from maize and rRNA promoters. Examples of promoters are described in Hanley-Bowdoin and Chua, TIBS (1987) 12: 67–70; Mullet et al., Plant Molec. Biol. (1985) 4: 39–54; Hanley-Bowdoin (1986) PhD. Dissertation, The Rockefeller University; Krebbers et al., Nucleic Acids Res. (1982) 10: 4985–5002; Zurawski et al., Nucleic Acids Res. (1981) 9: 3251–3270; and Zurawski et al., Proc. Nat'l Acad Sci. U.S.A. (1982) 79: 7699– 7703. Other promoters may be identified and the relative strength of promoters so idenntified evaluated, by placing a promoter of interest 5' to a promoterless marker gene and observing its effectiveness relative to transcription obtained from, for example, the promoter from the psbA gene, the strongest chloroplast promoter identified to date. The efficiency of foreign gene expression additionally may be enhanced by a variety of techniques. These include the use of multiple promoters inserted in tandem 5' to the DNA sequence of interest, for example a double psbA promoter, the addition of enhancer sequences and the like.

For the most part, promoters functional in the chloroplast are constitutive rather than inducible. However, where it is desired to provide for inducible expression of the polypeptide of interest, a regulatable promoter and/or a 5'untranslated region containing sequences which provide for regulation at the level of transcription and/or translation (at 3' end) may be provided. Transcription and RNA stability appear to be important determinants of chloroplast gene expression. For example, the 5' untranslated region may be used from a gene wherein expression is regulatable by light. Similarly, 3' inverted repeat regions could be used to stabilize RNA of foreign genes. Regulatable genes may be identified by enhanced expression in response to a particular stimulus of interest and low or absent expression in the absence of the stimulus. For example, a light regulatable gene may be identified where enhanced expression occurs during irradiation with light, while substantially reduced expression or no expression occurs in the negligible of light.

The DNA sequence encoding the polypeptide of interest may be a structural gene or a portion thereof which provides for a desired expression product. The gene may be any gene, whether native, mutant native, or foreign to the plant host. By foreign is intended a gene not endogenous to the host cell, but may include indigenous sequences, such as viral sequences and bacterial sequences which are naturally associated with the plant cell.

For native and mutant native genes, the gene may provide for increased capability of amino acid synthesis, enhanced response to light, herbicide resistance, for example, to glyphosate or atrazine, improved drought resistance, insect resistance (BT toxin gene), altered fatty acid synthesis, such as an increase in unsaturated fatty acids, enhanced fixation of $CO_2$. Foreign genes may include enhancement of native capabilities, herbicide resistance, resistance to various pests, such as viruses, insects, bacteria or fungi, production of foreign products, as a result of expression of one or more foreign genes, or the like. Mutant native genes include 16 SrRNA or its renal RNA gene, the altered native gene provides resistance to antibiotics, and a mutant rbcL (ribulose biphosphate carbonylase/oxygenase, large subunit. The altered native rcbL gene encodes a more active carbonylase which can enhance plant productivity.

In many instances, it will by desirable to have at least one additional structural gene such as a gene providing for antibiotic resistance or functional portion thereof to serve as a marker associated with the expression cassette. Those plant cells in which the foreign gene has been stably introduced can be detected by means of the marker gene. Of course, one may provide for a string of expression constructs having a plurality of the same or different genes in the construct. Thus the presence of only two genes is merely illustrative. As markers, for structural genes, one can employ β-lactamase, herbicide resistance genes such as a mutant psbA gene or EPSPS-aroA. Other markers can include the cat gene, which encodes chloramphenicol acetotransferase and the uidA gene which encodes β-glucuronidase (gus).

The DNA sequence encoding the polypeptide of interest may be synthetic, naturally derived, or a combination thereof. Depending upon the nature of the DNA sequence of interest, it may be desirable to synthesize the sequence with chloroplast preferred codons. The chloroplast preferred codons may be determined from the codons of highest frequency in the proteins expressed in the largest amount in the particular plant species of interest. Depending upon the desired applicability of transforming the chloroplast genome, the DNA sequence may be inserted relative to the promoter in either the sense or the antisense direction.

The termination region which is employed will be primarily one of convenience, since the termination region appears to be relatively interchangeable among chloroplasts and bacteria. The termination region may be native to the transcriptional initiation region, may be native to the DNA sequence of interest, or may be obtainable from another source. Convenient termination regions are available from. (See, for example, Chen and Orozco, *Nucleic Acids Res.* (1988) 16: 8411).

The transcription level in the chloroplast should be sufficient to provide sufficient RNA capable of resulting in a modified chloroplast. A "modified chloroplast" is a chloroplast having a detectably different phenotype from a chloroplast of the same species which has not been transformed or expressing a foreign gene product, that is, one not containing the expression cassette in question. Various changes in phenotype are of interest and include modification or alteration of native capabilities (either enhancement or diminution), absence of a native capability (for example, as the result of transformation using antisense sequences) or addition of a new capability. Examples include a chloroplast containing a mutant psbA gene and as a result capable of resistance to the herbicide atrazine or a chloroplast containing a foreign gene product such as EPSP synthase and thereby capable of resistance to the herbicide glyphosate or expressing a BT toxin gene and capable of resistance to worms and insects.

Where it is desired to obtain replication of a plasmid containing the expression cassette in the chloroplast any chloroplast origin of replication may be used in the expression construct.

The expression cassettes may be transformed into a plant cell of interest by any of a number of methods. These methods include, for example, biolistic devices (See, for example, Sanford, *Trends In Biotech.* (1988) 6: 299–302, U.S. Pat. No. 4,945,050; electroporation (Fromm et al., *Proc. Nat'l. Acad. Sci.* (*USA*) (1985) 82: 5824–5828); use of a laser beam, electroporation, microinjection or any other method capable of introducing DNA into a chloroplast. The use of these techniques permits the application of the invention described herein in a wide variety of both monocotyledonous and dicotyledonous plant cells.

For use in the bombardment transformation technique, an expression cassette is adsorbed to a bombardment particle, typically consisting of tungsten particle having an average size of about 0.7 µm. Particles consisting of other metals having a density similar to tungsten may also find use, such as gold, platinum and the like. Typically, about 2–5 µg of DNA is adsorbed per µg of tungsten, usually about 2 µg of DNA per µg of tungsten. Following adsorption of the DNA to the particles, any clumps of particles are dispersed, for example, by sonication. Any method to fix the DNA on the outside surface of the metal bombardment particles is acceptable and are known to those skilled in the art. (See, for example, Sanford et al. (1988) supra and Klein et al. supra). The DNA must be secured to the particles for delivery, but not fixed in such a manner as to impede release of the DNA into the cell.

For transformation, about 100–500 µg, generally approximately 200 µg of bombardment particles to which the expression cassette has been adsorbed are loaded into a particle gun (such as those available from Biolistics, Inc. and DuPont) according to the manufacturer's directions. Isolated cells generally 100–300 µg fresh weight per petri plate (5 cm diameter) are placed on a growth surface, such as a petri dish or tissue culture dish containing for example Whatman #1 filter paper with growth medium to adhere the cells to a solid surface. The cells do not have to be in a single cell layer, but may be a few layers thick. The immobilized cells are placed in the bombardment chamber of the particle gun and placed under as high a vacuum as feasible, generally about 0.07 to 0.3 atmospheres, preferably 0.07. The pressure in the sample chamber is then reduced to about 0.07 atmospheres prior to bombardment. The cells preferably are bombarded about 10 cm from the end of the barrel of the particle gun (at the fourth level in the DuPont gene gun). The firing mechanism of the particle gun is activated and the cells are bombarded from 1–3 times, generally twice to increase the number of transformed cells. The vacuum is then released, and the bombarded cells placed in fresh growth medium at about 26° C. preferably in the light in growth chambers. Other biolistic devices include the use of "flying discs" such as those made from plastic membranes or discs made of, for example nylon mesh (94 µm) ("helium entrainment" method).

A plant containing transgenic chloroplasts may be generated when the host cell used in the transformation process possesses totipotency. Procedures for regeneration of transgenic plants from transformed cells or tissues are, in general, similar, with suitable modifications within the capability of one skilled in the art. Regeneration of diciots such as sugar beets, Freytag et al. *Plant Cell Rep.* (1988) 7: 30–34; tobacco, Svab et al. *Proc. Nat'l Acad. Sci. U.S.A.* (1990) 8526–8530 or monocots such as wheat from anthers or embryos (see below) routinely has been successful.

If it is desired to transform chloroplasts in other plant materials, for example anther culture derived plants or embryo derived callus, the plant material is placed in a convenient container, for example a petri dish as described above for isolated cells.

The presence of the desired gene in the plant chloroplast can be established in a variety of ways, depending upon the nature of the gene. Techniques such as the Northern blot can be employed for detecting messenger RNA which codes for the polypeptide of interest. In addition, the presence of expression can be detected in a variety of ways. Where the expression product provides a detectable phenotype, such as a novel phenotype or modification of an endogenous trait, the expression of the desired product may be determined by detecting the phenotype. Where a detectable phenotype is not available, antibodies specific for the mature product may be employed. The chloroplasts may be isolated in accordance with conventional ways, disrupted and the western or other technique employed to identify the presence of a desired product. The presence of a gene which produces an exogenous product may be detected by isolation and lysis of the chloroplast. The resulting cellular material may then be assayed for the exogenous product or the exogenous gene. The exogenous product may be detected by electrophoresis, chromatography, immunoassay or the like. The gene may be detected for example by hybridization using Southern blotting. The transient expression system, reported here, should facilitate studies on foreign gene expression, regulation, or DNA replication in plastids in vivo. Thus, an approach may be opened to major advances in genetic engineering of higher plant organelles.

Once the chloroplast has been shown to have been transformed, the cells of the plant may be used repeatedly for tissue culture, followed by a growth of callus tissue were desired or regeneration of a plant. Thus, the modified plant cell may be repetitively regenerated by use of cell and tissue culture. In some instances, proper propagation may be maintained from seed.

As a host cell, any of a number of plant cells may be employed such as sugar beet, tobacco, wheat, etc.; plant parts of interest include leaves (chloroplasts), flowers (chromoplasts), roots, such as tubers (amyloplasts); fruits (chromoplasts); sprouts (germinating seedlings), etioplasts); sea weeds/algae (chloro/chromoplasts).

Constructs containing a selectable marker when expressed in the chloroplasts (for example resistance to a herbicide such as glyphosate or atrazine) may when used in conjunction with another structural gene, be used to select for chloroplasts, cells or plants containing the constructs.

The described methods and compositions find particular use in providing an altered phenotype in plant chloroplasts, such as providing directly for herbicide resistance and the like. The constructs may provide a means for selecting cells and plants containing transformed chloroplasts, where a selectable chloroplast function is included in the construct.

The following examples are offered by way of illustration and not by limitation.

EXPERIMENTAL

Example I

Transient Foreign Gene Expression in Chloroplasts of Cultured Tobacco Cells After Biolistic Delivery of Chloroplast Vectors Construction of Chloroplast Expression Vectors.

A series of chloroplast expression vectors has been constructed using the promoter selection vector pKK232-8 (Pharmacia), which is a pBR322 derivative containing a promoterless cat gene. Restriction fragments of chloroplast DNA (cpDNA) containing the entire promoter region and 5' untranslated region of the psbA gene from spinach (pMP450, a gift from Wilhelm Gruissem, University of California, Berkeley) pHD306 or pea (pPPBX10218, a gift from John Mullet, Tex. A & M University) pHD312 or, alternatively, the rbcL and atpB promoter region from maize (pPBI1443, a gift from Antony Gatenby, E. I. DuPont de Nemours & Co., Wilmington, Del.) pHD103 have been individually inserted into the multiple cloning site (MCS) that exists 5' proximal to the promoterless cat gene. The strength of each promoter has been investigated by analyzing transient expression of cat in cucumber etioplasts, as described in Daniell and McFadden, *Proc. Nat'l Acad. Sci. U.S.A.* (1987) 84: 6349–6353.

To study cat expression in the cytosol, a 35S-CAT construct obtained from Abdul Chaudhury (Ethan Signer's laboratory, MIT) has been used. This is a 4.2-kilobase-pair (kbp) plasmid designated pUC8CaMVCATψN, with a cat gene driven by a 35S cauliflower mosaic virus promoter and flanked by a 3' Nos PstI fragment. For negative controls, pUC118 or pUC19 has been used in all experiments.

In Vitro Replication Studies.

A replication fraction containing RNA polymerase, DNA polymerase, DNA primase, and topoisomerase I activities was isolated from pea chloroplasts as described by Meeker et al. (*Molec. Cell. Biol.* (1988) 8: 1216–1223). The heparin-Sepharose fraction was used for in vitro replication reactions. Insertions of a variety of replicon fragments into chloroplast expression vectors is described below.

Bombardment of Suspension Cells with Microprojectiles.

To prepare tobacco NT1 cells for bombardment with microprojectiles, about 100 mg of 4-day-old suspension cells (fresh weight) was collected on filter paper (Whatman no. 1. 5.5 cm) by vacuum filtration of 5 ml of suspension culture ($1 \times 10^6$ cells per ml). Two layers of filter paper were placed inside a 5.5-cm Petri dish and moistened with 1.4 ml of MS medium (Murashige and Skoog *Physiol. Plant.* (1962) 15: 473–497). The single filter paper bearing the cells was then placed over the two layers of filter paper.

Tungsten particles coated with DNA were prepared essentially as described by Boynton et al. (*Science* (1988) 240: 1534–1538). To adsorb DNA to the microprojectiles, 2.5 μl of DNA (1 μg/μg of TE buffer containing 10 mM Tris HCl and 1 mM EDTA, pH 7.7) was added to 25 μl of a suspension of tungsten particles (0.05 mg/ml of 50% glycerol) in a 1.5-ml Eppendorf tube. After addition of the DNA, CaCl$_2$ (25 μl of a 2.5M solution) and spermidine free base (5 μl of a 1M solution) were added to the suspension. After 10 min of incubation, the particles were pelleted by centrifugation in a Microfuge for 30 sec. and a portion of the supernatant (25 μl) was removed. The final microprojectile preparation therefore contained 39 μg of tungsten per μl of suspension and 2 μl of DNA per μl of tungsten. The clumps of particles were dispersed by briefly (1 sec) touching the outside of the Eppendorf tube to the probe of a sonicator. After sonication, 5 μl of the tungsten/DNA suspension was placed on the front surface of a cylindrically shaped polyethylene macroprojectile. The macroprojectile was then placed into the barrel of the particle gun and accelerated.

Cells were bombarded 10 cm from the end of the barrel of the particle gun. The pressure in the sample chamber was reduced to 0.1 atmosphere prior to bombardment. In all experiments, three replicate Petri plates were bombarded per treatment. After the addition of fresh growth medium, the cells were maintained at 25° C. in the light, in plant growth chambers.

Analysis of cat Expression in NT1 Cells and Protoplasts.

Cultured tobacco cells were transferred to Corex tubes and washed once with 10 ml of TE buffer containing 250 mM Tris HCl and 10 mM EDTA (pH 7.8). Cells centrifuged at 8000 X g for 10 min were transferred to 2-ml Eppendorf tubes and resuspended in 1 ml of TE buffer (pH 7.8) containing 2 mM phenylmethylsulfonyl fluoride. The cells were sonicated twice for 20 sec each, using a probe sonicator. After a 15-min centrifugation at 4° C., the supernatants were transferred to new Eppendorf tubes and assayed for cat activity as described in Daniell and McFadden, supra. NT1 protoplasts were prepared and electroporated as described by Paszty and Lurquin (*Biotechniques* (1987) 5: 716–718) except that the 250 µF capacitor was charged to 250 V and 1.5 million protoplasts were used per electroporation event.

Expression of Foreign Genes in Isolated Chloroplasts

The cucumber etioplast in organello transient expression system (See Daniell and McFadden, supra) was used to test the strength of chloroplast promoter fragments inserted into the MCS 5' proximal to the promoterless cat gene (FIG. 1). Transient expression of cat in EDTA-washed etioplasts isolated from hormone-pretreated cucumber cotyledons revealed spinach or pea psbA promoter (pHD306, pHD312) to be the strongest among the promoter fragments tested. Since expression studies after bombardment of foreign DNA were planned to be conducted in nonphotosynthetic cells, the transient expression system in etioplasts served as an analogous comparable system to the plastids present in cultured tobacco cells.

In Vitro Replication of Chloroplast Expression Vectors.

Figure 2:
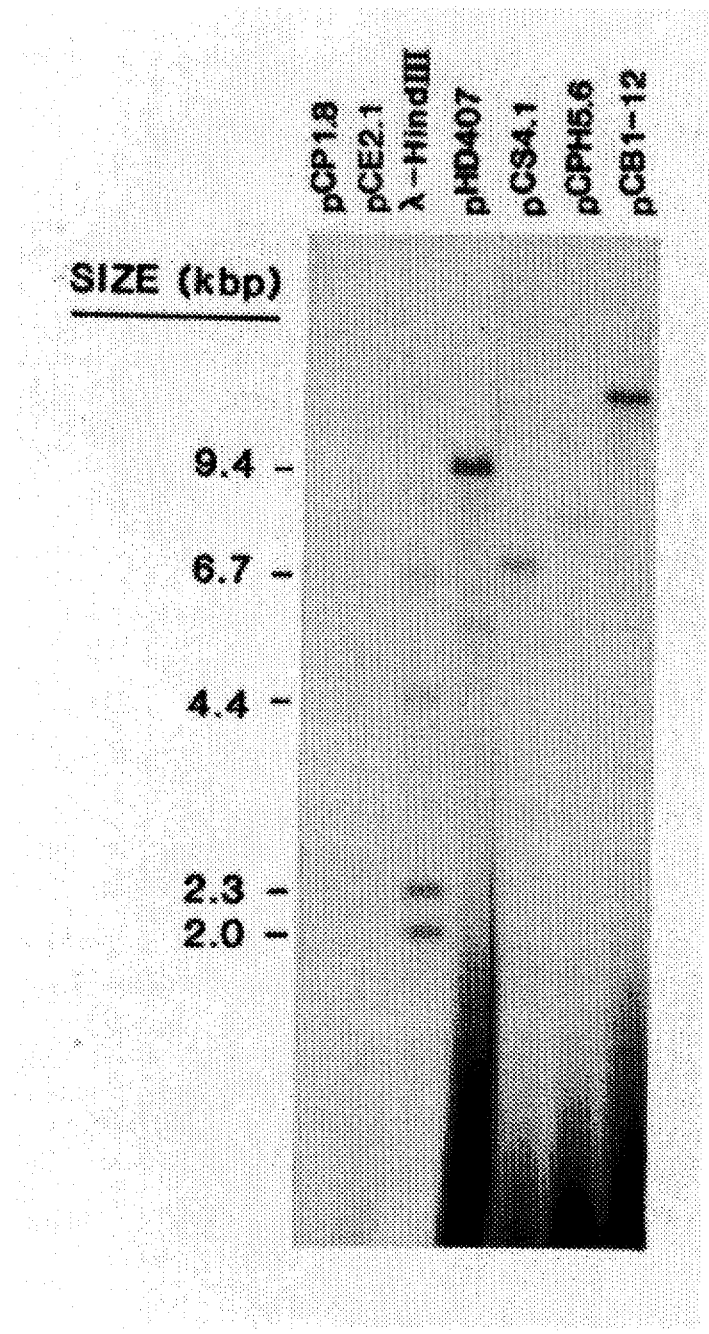
FIG. 2 shows alkaline agarose gel of in vitro replication products. In vitro replication reactions were carried out as described in ref. 20. After phenol extraction and ethanol precipitation, the samples were separated in a 0.8% alkaline agarose gel, and the gel was dried and autoradiographed. Phage λ DNA markers were digested with HindIII and 5' end-labeled with [α-$^{32}$P]ATP and polynucleotide kinase.

Plasmid construction pCB1-12 is a 10-kbp BamHI pea cpDNA fragment in pBR322, containing both D-loop regions (See Tewari et al., supra). The plasmid pCPH5.6 is a 5.6-kbp PstI-HindIII cpDNA fragment in pUC19 containing one of the two D-loop regions. The plasmid pCE2.1 is a 2.1-kbp EcoRI cpDNA fragment from the region between the two replication origins. Plasmid pCP1.8 is a 1.8-kbp PsiI clone from a distant region of the cpDNA. All of these constructions were used as templates for in vitro DNA synthesis using a replication fraction isolated from pea chloroplasts, and the in vitro replication products were analyzed on alkaline agarose denaturing gels. As seen in FIG. 2, the autoradiogram showed lack of synthesis of any full-size DNA molecule in pCP1.8 and pCE2.1, which do not contain a D-loop region; the autoradiogram clearly showed in vitro synthesis of single-stranded DNA molecules of about 14.5 and 6.3 kbp. corresponding to full-length pCB1-12 and pCS4.1, respectively. The 4.1-kbp SmaI fragment in pCS4.1, found to be active in in vitro DNA synthesis, was inserted into the chloroplast expression vector pHD312, which contains the pea psbA promoter 5' proximal to the cat gene. The resultant construction, pHD407, when analyzed for in vitro DNA synthesis, appeared as a single-stranded DNA molecule of about 9.9 kbp in an alkaline agarose denaturing gel (FIG. 2).

Expression of cat in Tobacco NT1 Suspension Cells.

Figure 3A:
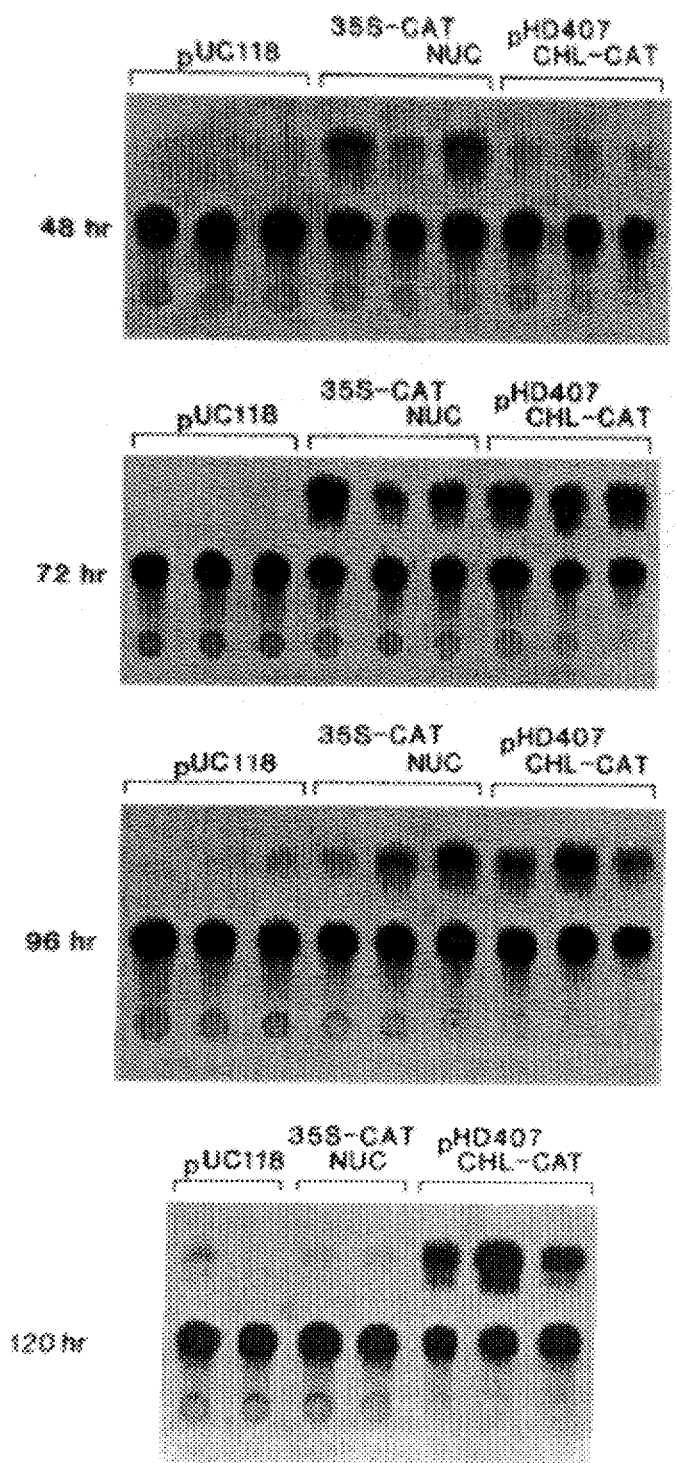
FIG. 3 shows (a) analysis of cat expression in tobacco NT1 suspension cells bombarded with pUC118 (negative control), 35S-CAT (nuclear expression vector), and pHD407 (chloroplast expression vector containing chloroplast replicon). The average protein concentrations in 500 µl of the samples assayed are as follows. 48 hr: pUC118, 900 µg; 35S-CAT, 476 µg; pHD407, 870 µg; 72 hr: pUC118, 787 µg; 35S-CAT, 590 µg; pHD407, 710 µg; 96 hr: pUC118, 360 µg; 35S-CAT, 147 µg; pHD407, 48 µg; 120 hr: pUC118, 523 µg; 35S-CAT, 91 µg; pHD407, 99 µg. (b) Analysis of cat expression in tobacco NT1 suspension cells bombarded with chloroplast expression vectors containing various replicon fragments and promoters. Protein concentration in samples assayed (72 hr after bombardment) are as follows. (upper) pUC118: 856, 1008 µg; pHD312 (repliconless): 802, 1075 µg; pHD407 (pea replicon): 1075, 488 µg; 35S-CAT: 1160, 1102 µg. The film was exposed to the TLC plate for 8 hr. (Lower) pUC118; 65, 62 µg; pHD312: 40, 46 µg; pHD407; 32, 26 µg; 35S-CAT; 39, 38 µg; rbcL-CAT (tobacco replicon): 276 µg; rbcL-CAT (maize replicon): 275 µg; rbcL-CAT (no replicon): 248 µg. The film was exposed to the TLC plate for 4 days due to the low number of bombarded cells.

Expression of cat was assayed in sonic extracts incubated in the presence of (dichloroacetyl-1-$^{14}$C)chloramphenicol and acetyl coenzyme. Sonic extracts of cells bombarded with pUC118 showed no detectable cat activity in the autoradiograms; cells bombarded with 35S-CAT showed maximal expression 72 hr after bombardment, whereas those bombarded with pHD407 and pHD312 showed a low level of expression until 48 hr of incubation (FIG. 3A). A dramatic increase in the expression of cat was observed 24 hr after the addition of fresh medium to cultured cells in samples bombarded with pHD407.

Figure 4:
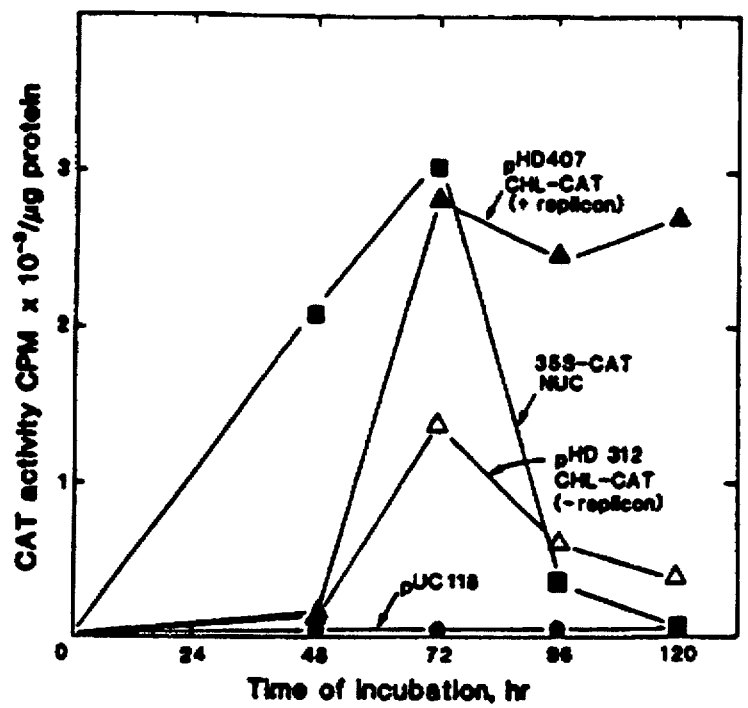
FIG. 4 shows quantitative expression of cat in tobacco Nt1 suspension cells assayed with identical protein concentrations in sonic extracts. After autoradiography of the separated acetylated chloramphenicol forms for 4 hr. spots were scraped and radioactivity was counted. Silica gel alone had a background of 2203 cpm; the ranges of cpm between different samples were as follows: pUC19, 2705–6556 cpm; 35S-CAT, 3993–220, 353 cpm; pHD312, 2410–133, 240 cpm; pHD407, 7484–267, 364 cpm.

The repliconless chloroplast expression vector pHD312 showed maximal activity at 72 hr of incubation, which is about 50% of the activity observed with pHD407 at that time point (FIG. 4). A high level of cat expression was maintained with subsequent incubation of cultured cells bombarded with pHD407, whereas the expression of nuclear cat and the repliconless chloroplast vector sharply declined. Quantitative studies confirmed the earlier visual observation (FIG. 4). These results suggest that the "biolistic" process delivers foreign DNA into chloroplasts of cultured tobacco cells and that the marker gene is expressed in appropriate compartments. The kinetics of cat activity, as a function of incubation time after bombardment, may be interpreted as an indication that the delivery process into the chloroplast is not as efficient as into the nucleus since expression of all chloroplast vectors is delayed until 72 hr. Chloroplast vectors with the replicon (pHD407) may subsequently replicate autonomously inside the chloroplasts, resulting in a higher level of expression. However, the contribution of the upstream promoter sequences of 23S rRNA gene, present in the replicon fragment in pHD407, to enhanced transcription/ translation of the cat gene cannot be ruled out.

Figure 3B:
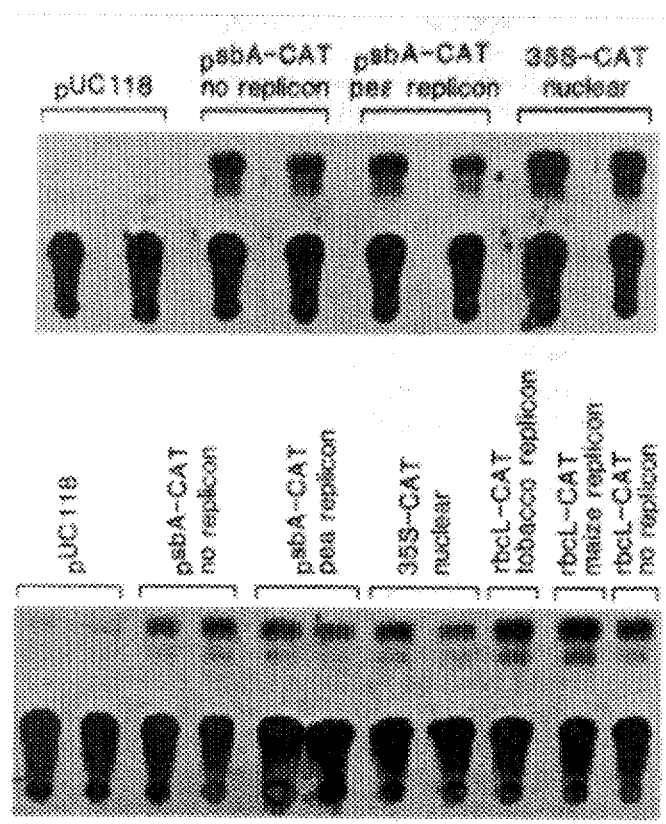

These observations were subsequently confirmed by investigations using similar chloroplast expression vectors provided by L. Bogorad's laboratory. Expression of cat was studied in NT1 cells bombarded with vectors containing replicon inserts from tobacco and maize chloroplast genomes (FIG. 3B). A tobacco Bam4 cpDNA fragment was cloned into pGV825 (a Ti plasmid intermediate vector) to produce pACp18; this fragment cloned into pUC supports DNA synthesis in vitro using the replication system described by Carrillo and Bogorad (*Nucleic Acids Res.* (1988) 16: 5603–5620). Maize Bam10 fragment was cloned into pGV825 to produce pACp19; this fragment cloned into pBR322 is not especially active in the in vitro DNA synthesis assay of Tewari and co-workers (*Proc. Nat'l Acad. Sci. U.S.A.* (1987) 84: 194–198) but functions as an autonomously replicating sequence in yeast (when cloned into YPI5). The repliconless vector showed $0.74 \times 10^3$ cpm cat activity per µg of protein in sonic extract of cells 72 hr after bombardment; vectors containing replicon fragments from tobacco and maize showed 1.03 and $1.45 \times 10^3$ cpm per µg of protein, respectively. In all of these constructs, the bacterial cat gene is under the control of an rbcL promoter region from maize.

Sterility tests to ensure absence of microbial contamination of the cultures were performed by streaking an aliquot of cells or protoplasts on LB agar plates, for every time point, after bombardment or prior to sonication. Among the cat assays presented in FIG. 3A, two contaminants were noticed. These samples were discarded and hence fewer cat assays have been presented for the last time point. No bacterial contamination has been observed in other batches of bombarded cells. Expression studies have been performed in six different batches of cells, varying several parameters.

Figure 5:
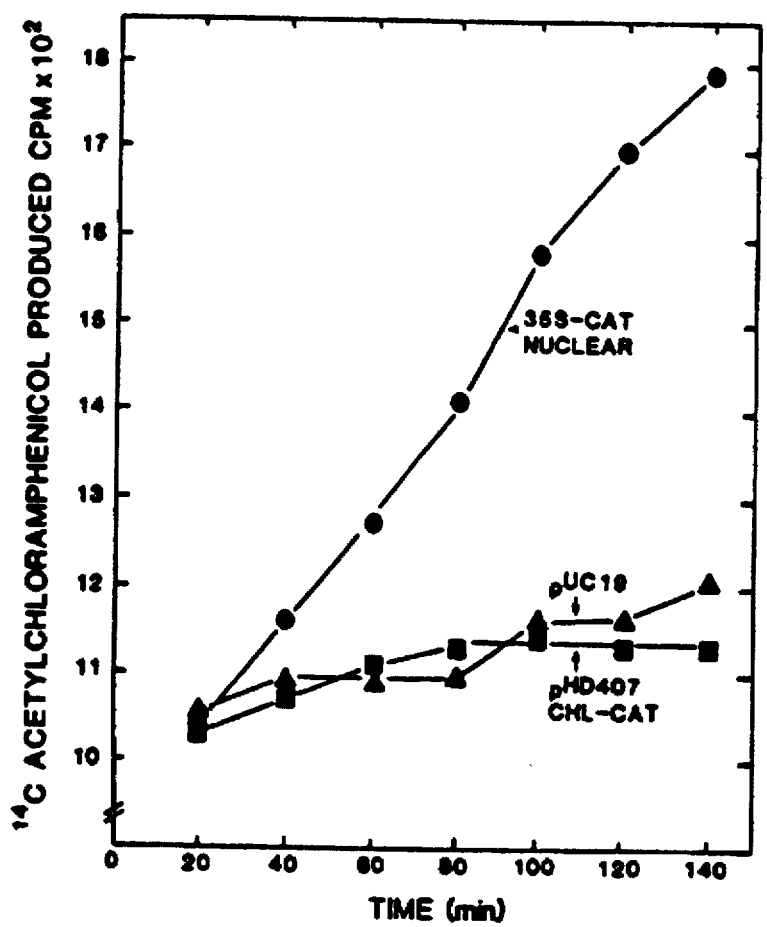
FIG. 5 shows kinetics of chloramphenicol acetylation with [$^{14}$C]acetyl CoA, in tobacco NT1 protoplasts eletroparated with foreign DNA. Pelleted protoplasts were resuspended in (400 µl) extraction buffer (5 mM EDTA/0.25M Tris-HCl, pH 7.8, and 1.0 µg each antipain and pepstatin per ml), sonicated for 20 sec, and centrifuged in a Microfuge for 5 min at 4° C. to pellet the debris. The extract (190 µl) after heat treatment (65° C., 10 min) was mixed with [$^{14}$C]acetyl CoA (0.1 µCi; 1 Ci=37 GBq) and chloramphenicol (40 µl of 8 mM stock). The reaction was carried out at 37° C. using the highly quantitative two-phase assay system described by Neumann et al (26). Slope values derived from data points and DNA concentrations used for eletroporation were as follows: pUC19, 31.0 (15 µg); pHD407, 24.2 (50 µg); 35S-CAT, 114.1 (15 µg). The correlation coefficient varied between 0.9 and 0.99 for different sets of experiments.

Organelle-specific expression of cat in appropriate compartments was checked by introducing all three plasmid constructions, pUC19, 35S-CAT, and pHD407, into tobacco protoplasts by electroporation (FIG. 5) and assaying using the highly quantitative two-phase assay system (Neumann et al., *Biotechniques* (1987) 5: 444–447). Although 35S-CAT showed expression of cat, no activity was observed with pUC19 and pHD407, establishing the fact that these two constructions do not express in the nucleus. It is known that electroporation of protoplasts delivers DNA into the cytosol but not inside organelles. Furthermore, recent attempts to induce tobacco psbA promoter to function in the nuclear compartment (to study transient expression of bar or nptII genes) revealed the absolute need to insert 35S promoter or enhancer elements 5' proximal to the psbA promoter region (Cornelissen and Vandewiele, *Nucleic Acids Res.* (1989) 17: 19–29). Bogorad and co-workers also observed that chloroplast genes were not transcribed from their own promoters when placed in the nuclei of transgenic tobacco plants (Cheung et al., *Proc. Nat'l Acad. Sci. U.S.A.* (1988) 85: 391–395).

Example II

Figure 6:
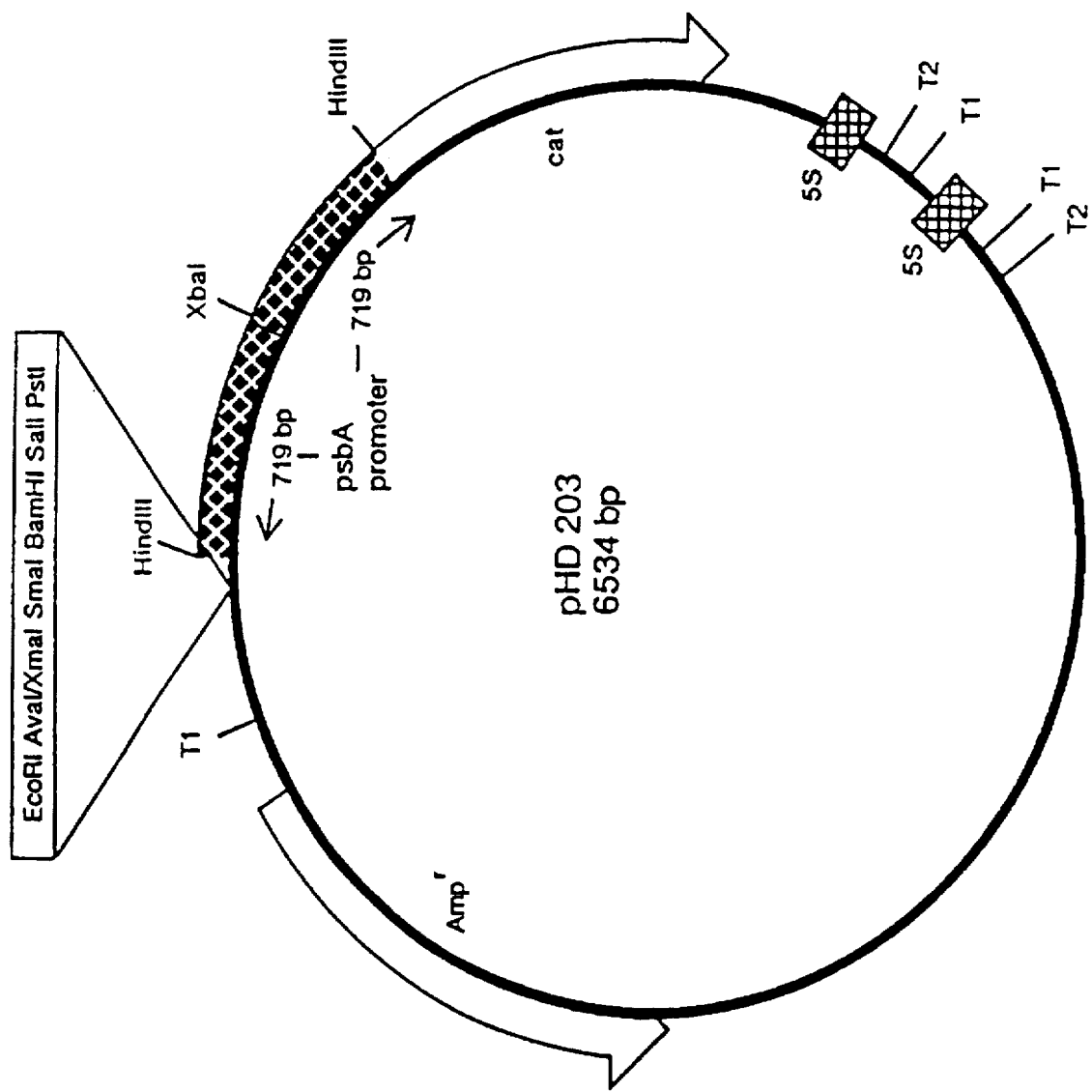
FIG. 6 shows Chloroplast Expression Vector pHD203. This vector contains a double psbA promoter inserted in opposite orientations to facilitate insertion of additional genes. E. coli uidA gene coding for β-glucuronidase has been inserted into the MCS.

Transient Foreign Gene Expression in Different Cellular Components of Wheat Leaves and Calli After Biolistic Delivery Construction of the Chloroplast Expression Vector, pHD203-GUS The chloroplast expression vector pHD203 (FIG. 6), a pBR322 derivative, contains a double psbA promoter fragment (from the pea chloroplast genome) inserted in opposite orientations to facilitate simultaneous transcription of two promoterless genes. One of the two psbA promoter regions drives the cat gene. The presence of ribosomal RNA T1 and T2 terminators distal to the cat gene aids transcription termination, while the presence of three stop codons between the psbA promoter and the AUG of the cat gene prevents translational readthrough into the cat gene. The second psbA promoter fragment has been placed upstream of a multiple cloning site (MCS) containing sites for EcoRI, AvaI, XmaI, SmaI, BamHI, SalI, HincII, PstI and HindIII. There is a ribosomal RNA T1 terminator distal to the MCS to aid transcription termination. There are convenient EcoRI and PstI sites within the cat and β-lactamase genes, respectively, to screen for partial digestion of pHD203. The *E. coli* uidA gene coding for β-glucuronidase (GUS) (Jefferson et al., *Proc. Nat'l Acad. Sci. U.S.A.* (1986) 83: 8447–8451) was inserted into the MCS of pHD203 (FIG. 6.). The following restriction sites originally present in pHD203 have been lost in pHD203-GUS: HindIII (208 in PHD203), HincII (196), SalI (194), BamHI (188) and SmaI (185). Restriction analyses were done to confirm proper construction before proceeding with studies on the expression of GUS.

Nuclear Expression Vector pBI 121

The nuclear expression vector pBI121 (Dr. J. C. Sanford) carries a GUS gene driven by a CaMV-35S promoter and flanked at the 3' end by a nos terminator and a polyA tail (Jefferson, *Plant Mol. Biol. Rep.* (1987) 5: 387–405). For negative control, pUC19 DNA was routinely used in all bombardments.

Plant Materials

Green and albino plants were obtained from anther culture (Zhou and Konzak, *Crop Sci.* (1989) 29: 817–821) of wheat cultivars 'Edwall', 'Payon 76' and 'Payon 808'. When the plants were at the 2–3 leaf stage, they were transplanted aseptically into test tubes containing half strength MS media (Murashige and Skoog, (1962) supra, supplemented with 2% sucrose and solidified with 0.8% agar. Calli were regenerated from immature embryos of wheat by a modified method of Sears and Deckard *Crop Sci.* (1982) 22: 546–551. The 10–12 days old immature embryos were placed on basal MS media containing only half the amount of 2–4 D (1 mg/l); the calli were maintained in this medium until hard white embryogenic tissue developed. This tissue usually starts forming after about 2 months when the calli are transferred to fresh media every 3–4 weeks. Calli rich in this tissue were transferred to fresh media and used for bombardment.

Bombardment of Wheat Leaves or Calli With Microprojectiles:

Tungsten particles (60 mg, M-10) were soaked overnight in 1 ml of absolute ethanol, after vortexing for 2 min. After washing thrice with autoclaved water, the particles were resuspended in 50% glycerol (sterile). Particles for bombardment were prepared as follows: 25 ul of washed particles was added to 5 ug of DNA in TE (10 mM Tris, 1 mM EDTA, pH 8.0) buffer followed by the addition of 25 ul of $CaCl_2$ (2.5M) and 5 ul of spermidine (1M). After incubating the DNA with the tungsten particles for 10 min at room temperature, 40 ul of the supernatant was discarded after a brief centrifugation. Five ul of the remaining DNA coated tungsten particles was loaded onto the macroprojectile. Prior to bombardment, anther culture-derived green or albino plants or embryo derived calli were placed in petri dishes (10 cm in diameter) in MS salts (36) containing 2% sucrose, solidified with 0.8% agar. Keeping the samples at the fourth level in DuPont's gene gun PDS-1000 and vacuum at 0.07 atmosphere, each sample was bombarded twice. In all experiments, triplicate samples were bombarded per treatment. After bombardment, the plant materials were incubated at 26° C. for 72 hrs in growth chambers. Contamination by bacteria was continuously monitored by checking tissues at various stages of the experiment and by bombarding plasmids that do not contain the GUS gene.

β-Glucuronidase Assay

Three days after bombardment, the tissues were assayed for GUS activity by adding suitable aliquots of the GUS substrate that contained 0.5 mg/ml 5-bromo-4 chloro-3-indoyl-B-D-glucuronic acid, and 0.1% of Triton X-100 10 mM EDTA, 0.5 mM potassium ferrocyanide in 100 mM sodium phosphate buffer, pH 7.0. The Petri dishes were then sealed with Parafilm and incubated at 37° C., overnight; cells or tissues were observed under the microscope and photographed.

Figure 7A:
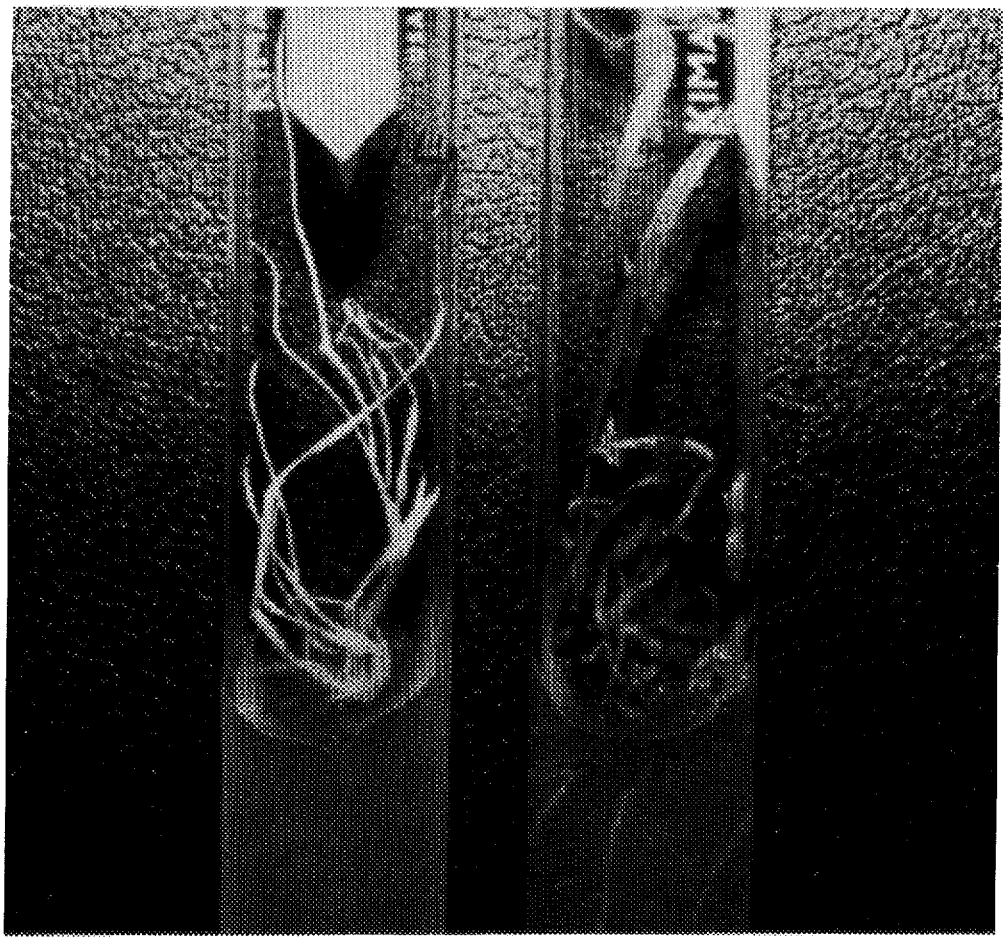
FIG. 7 shows foreign gene expression studies in anther derived green and albino plants. (a) Green and white albino wheat plants regenerated from anther culture. (b) Expression of GUS in the albino wheat leaf bombarded with pHD203-GUS (top) and lack of expression in the leaf bombarded with pUC 19 (bottom). (c) Expression of GUS in the green wheat leaf bombarded with pBI121 (middle), pHD 203-GUS (right); note the lack of GUS expression but the presence of tungsten particles in the plant bombarded with pUC19 (left). (d) Microscopic observation of GUS expression in cells from a green leaf bombarded with pBI121. Note the presence of GUS cleaved product spread evenly all around the cytosol. (e, f) Subcellular localization of GUS expression in chloroplasts of cells from a green leaf bombarded with pHD203-GUS. Note green, blue green and green plastids present inside the cells. (g, h) Foreign gene expression studies in wheat callus derived from immature embryos: Calli were bombarded with G) pUC19 H) pHD203-GUS. Note tungsten particles at the site of bombardment and the smaller blue spots scattered all around the callus bombarded with pHD 203-GUS.

GUS Expression in Anther Derived Albino Plants:

FIG. 7A shows the GUS was expressed in the albino leaf bombarded with pHD203-GUS (left) but not in that bombarded with pUC19 (right). The product of uidA gene, β-glucuronidase, when present, cleaves β-glucuronic acid from the substrate X-gluc (5-bromo-4-chloro-3-indoyl-B-D-glucuronic acid) to produce an insoluble indigo dye following oxidative dimerization. Even though some of the earlier investigations on pollen derived albino rice plants indicated lack of ribosomes in albino plastids as the cause of albinism (Sun et al., *Theor. Appl. Genet.* (1979) 55: 193–197, subsequent studies in other laboratories observed alterations in the albino plastid genome (Day and Ellis, *Cell* (1984 39: 359–368, and Current Genet. (1985) 9: 671–678. Our recent studies have unequivocally established the presence of a functional transcriptional/translational machinery in the plastids of anther culture derived albino wheat plants (data not shown). Expression of GUS in albino leaves bombarded with pHD203-GUS (FIG. 7A) further confirms observations of the presence of a functional protein synthetic machinery in albino plastids. Chloroplast specific expression of GUS by pHD203-GUS is discussed below in the section on "compartmentalized GUS expression".

GUS Expression in Anther Derived Green Plants:

Green plants derived from anther culture were preferred for studies on gene expression because the results are comparable to field grown plants but at the same time are free of bacteria since they had been grown under totally sterile conditions. Though the tungsten particles are seen in the sample bombarded with pUC 19 no GUS expression is observed. On the other hand, it is evident from samples bombarded with pBI121 and pHD203 that B-glucuronidase, when present, cleaved glucuronic acid from the substrate X-gluc to produce an insoluble indigo dye.

Figure 7B:
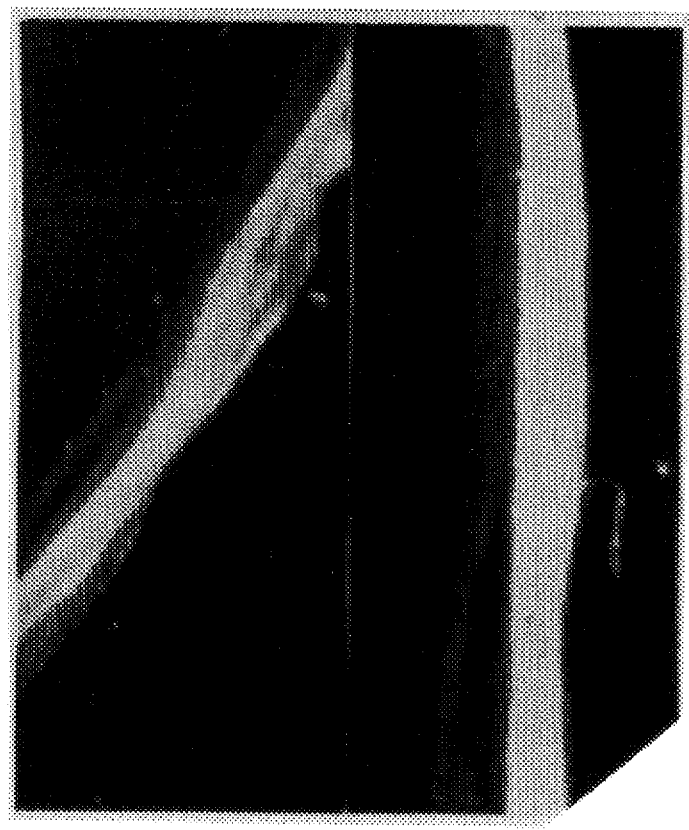
Figure 7C:
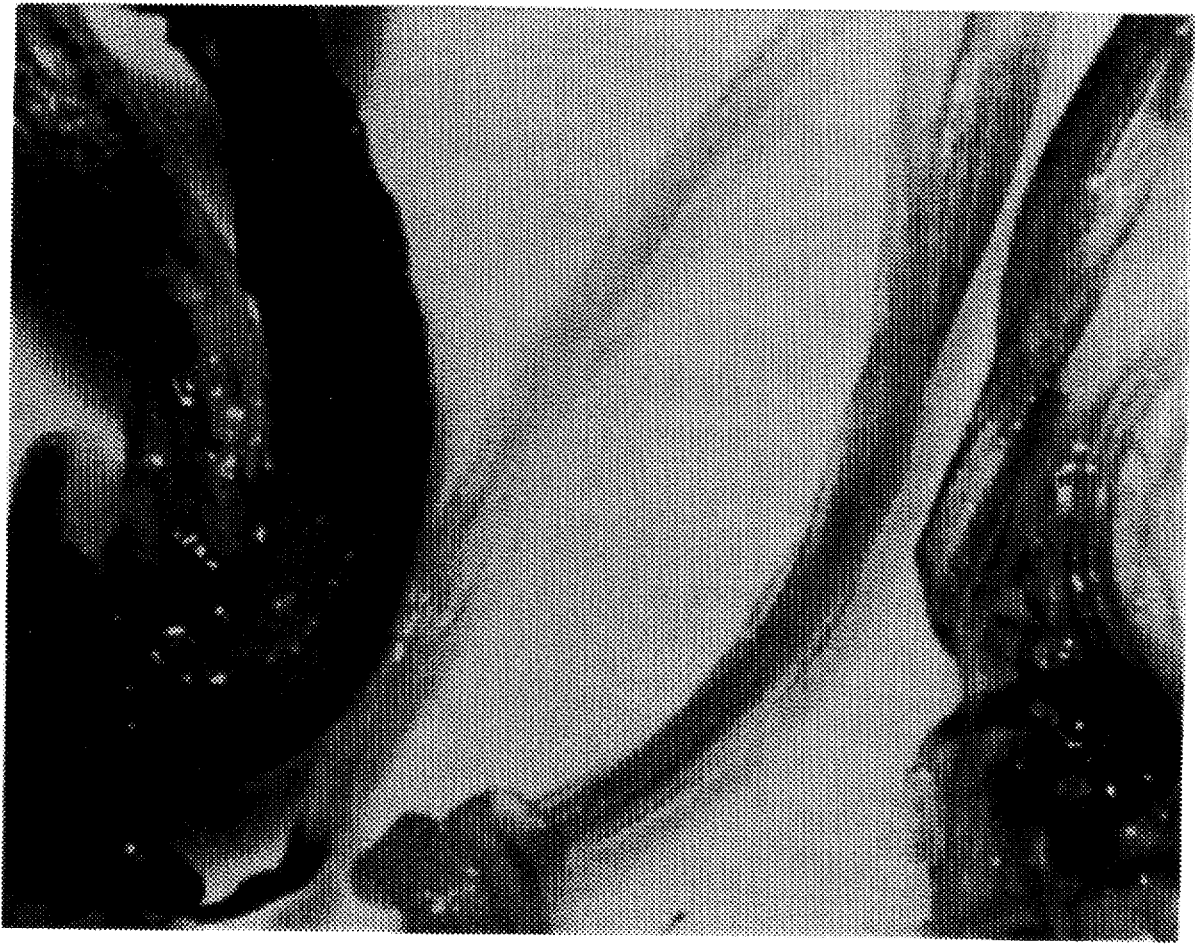
Figure 7D:
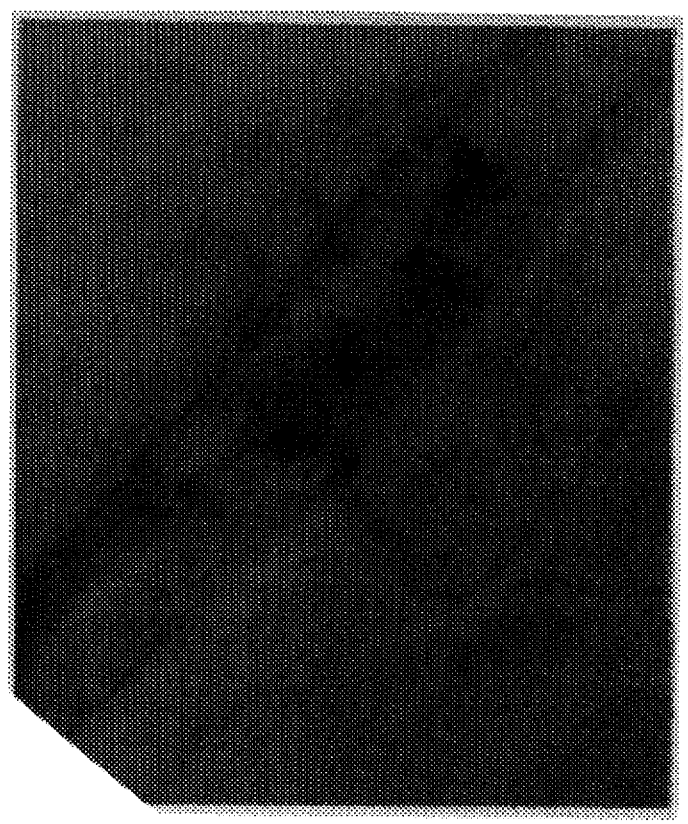

Compartmentalized GUS Expression:

In order to identify the precise compartment in which pBI121 or pHD203-GUS function, bombarded leaves from anther derived green plants were examined under the microscope. As shown in FIG. 7B, B-glucuronidase cleaved product, the indigo dye, was present evenly all around the cytosol, when nuclear expression vector pBI121 was bombarded into wheat leaves. When chloroplast expression vector pHD203-GUS was used for bombardment, the indigo dye was subcellularly localized within the chloroplasts of wheat cells (FIGS. 7C,D).

Chloroplast specific expression of pHD203-GUS has been confirmed by its failure to express when introduced into the cytosol of protoplasts by PEG-mediated transformation and distinctly different kinetics of expression than the nuclear vector and subcellular localization of the cleaved product in cultured NT1 tobacco cells (data not shown). These results also confirm earlier observations of the failure of CAT expression in tobacco NT1 protoplasts upon electroporation of chloroplast vectors containing the cat gene driven by a psbA promoter (Daniell et al., *Proc. Nat'l Acad. Sci. U.S.A.* (1990 87: 88–92). More recently, the precise localization of chloroplast vectors inside plastids of cultured sugar beet cells following biolistic delivery, using an in vivo DNA replication system (see above) has been demonstrated.

Figure 7E:
Figure 7F:
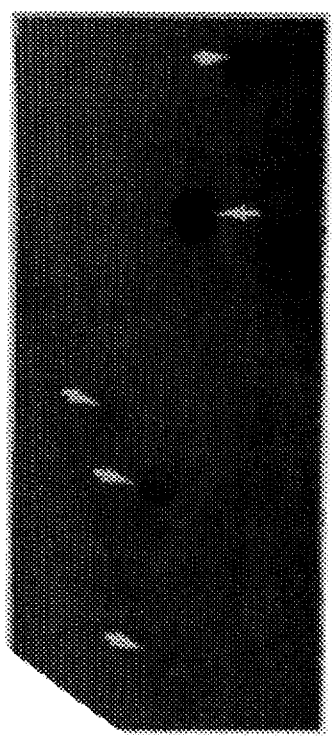
Figure 7G:
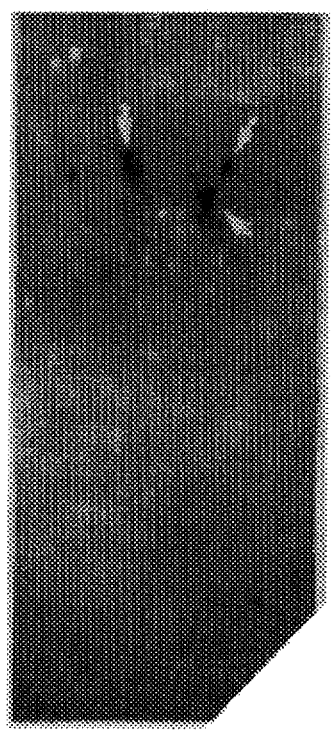
Figure 7H:
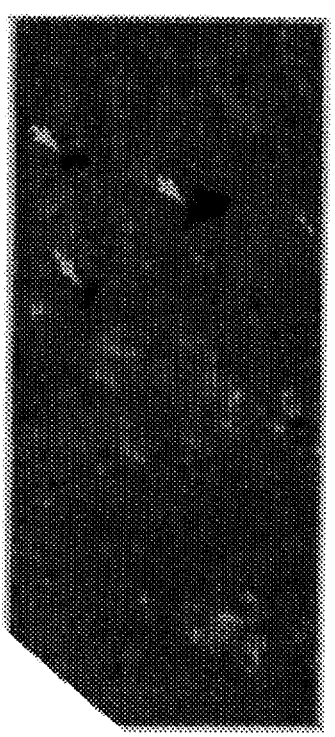

GUS Expression in Callus Derived from Immature Embryos:

While anther derived albino and green plants are ideal to study transient expression of foreign genes, regeneration of wheat plants from them may be a formidable challenge. Therefore calli rich in embryonic tissue were regenerated from immature embryos of wheat. FIG. 7E shows the expression of GUS in regenerable callus derived from immature embryos. When bombarded with foreign DNA, callus clumps were shattered upon impact from the tungsten particles; however, this did not affect their subsequent gene expression. No background indigo dye was detected in negative controls, bombarded with pUC19, when GUS substrate was added (FIG. 7F). Both large and small blue spots were observed in the callus bombarded with pHD203-GUS (FIG. 7F), indicating that chloroplasts in a number of targeted cells have been transformed.

Transient expression of GUS in different cellular compartments following biolistic delivery of chloroplast or nuclear expression vectors into wheat cells, leaves or calli, derived from anther culture or immature embryos, is reported here. Expression of GUS in albino plastids when albino leaves were bombarded with pHD203-GUS confirms the presence of a functional protein synthetic machinery in these organelles. When pBI121, the nuclear GUS vector was bombarded, the B-glucuronidase cleaved product was observed evenly all around the cytosol. When pHD203-GUS was bombarded, the indigo dye was subcellularly localized within the chloroplasts of wheat cells. GUS expression could also be observed in regenerable calli derived from wheat immature embryos. Lack of expression of GUS in negative controls bombarded with pUC19 was evident.

EXAMPLE III

Optimization of Delivery of Foreign DNA Into Higher Plant Chloroplasts

New Biolistic Device

The standard gun-powder driven PDS-1000 biolistic device (DuPont Co.) was compared to a newly designed helium driven device. Briefly, a small chamber is sealed at one end with one or more layers of rupturable membrane (2 mil plastic membrane). The chamber is then filled to high pressure with helium gas. A solenoid-driven lance then ruptures the membrane, which releases a sharply defined shock wave. The shock wave then enters a throat region of the device which contains a removable sleeve. Inside the sleeve are removable rings which are used to retain various microprojectile launching mechanisms. The principal mechanism employed in this paper is helium entrainment. In the helium entrainment configuration, a nylon mesh is locked into place across the axis of the sleeve. Microprojectiles (in suspension) are loaded directly onto the center of the mesh, and the helium shock wave atomizes and accelerates the microprojectiles as it passes through the mesh. A second mechanism employed involves acceleration of a flying disc. In this configuration, a plastic membrane is loosely held in the same position as the nylon mesh. Particles are dried onto its surface and upon firing, the disc is accelerated down the sleeve 1 cm, where it impacts against a screen stopping surface. The entire system is enclosed within a vacuum chamber.

Bombardment of Suspension Cells With Microprojectiles

To prepare tobacco NT1 cells (Paszty and Lurquin Paszty, supra) for bombardment with microprojectiles, about 100 mg of cells from a 4-day-old suspension were collected on filter paper (Whatman No. 1, 5.5 cm) by vacuum filtration of 5 mls of the suspension culture. Two layers of filter paper were placed inside a 60-mm petri dish and moistened with 1.5 ml of NTI medium (Paszty and Lurquin, supra. The single filter paper bearing the cells was then placed over the two layers of filter paper. The samples were bombarded with tungsten particles coated with DNA.

The DNA coating procedure was as described by Klein et al. except that after 10 min. of incubation of the DNA-tungsten suspension, the particles were pelleted by a pulse centrifugation in a microfuge, and the supernatant was removed. The pellet was washed once a 70 µl of 100% ethanol, pelleted and resuspended in 30 µl of 100% ethanol. 8 µl of the tungsten/DNA suspension was spread and dried on the center of 1 inch disc made of 2 mil plastic membrane (for 'flying disc' method), or a 1 inch disc of 94 µm nylon mesh (for 'helium entrainment' method).

For the 'flying disc' configuration, the flying disc was then loaded into a brass launch ring, which was screwed into a sleeve, with a metal screen on a retainer ring 1.3 cm below the brass launch ring. The flying disc had an effective flight distance of 1 cm. For the 'helium entrainment' configuration, the nylon mesh was trapped between two brass rings, which were screwed into the sleeve. The sleeve was then placed into the sleeve holder at the desired height. The rupture-end of the high pressure chamber of the gun was sealed with an appropriate number of isopropanol soaked 2 mil plastic rupture discs (3 layers for 900 psi; 4 for 1200 psi and 5 for 1500 psi). The target sample was loaded at a chosen platform height in the sample chamber, and bombarded under partial vacuum (0.3 atmosphere).

In all experiments, at least 3 replicate petri plates were bombarded per treatment. After bombardment, 0.5 ml fresh NT1 medium was added to each plate. The plates were sealed and incubated at 26° C. in the light. Two days after bombardment, an additional 0.4 ml of NT1 medium was added to each plate.

Polyethylene glycol (PEG)-Mediated Transformation of NT1 Protoplasts

NT1 protoplasts were prepared as described by Ye and Earle (submitted), except that 2% Cellulase-RS (Onozuka)

was used in place of CELF Cellulase in the enzyme solution. PEG transformation of protoplasts was performed according to Negrutiu et al., *Plant Molec. Biol* (1987) 8: 363–373. Protoplasts were cultured in NT1 protoplast culture medium Paszty and Lurquin, *Biotechniques* (1987) 5: 716–718 solidified with 1% Sea Plaque Low Melting Temperature agarose (FMC) in 60 mm petri dishes at room temperature in the dark.

β-Glucuronidase Assays

Three days after bombardment, cells were assayed for GUS activity by adding an aliquot of 1.5 ml of the substrate mixture as described by McCabe et al., *Bio/Technology* (1988) 6: 923–926. The petri dishes were then sealed and incubated at 37° C. overnight. The cells on the filter paper were observed with a microscope and the number of individual cells or aggregates of cells that developed blue color were counted. Transformation efficiency was expressed as number of blue spots per plate.

Chloroplast Expression of GUS

Figure 8:
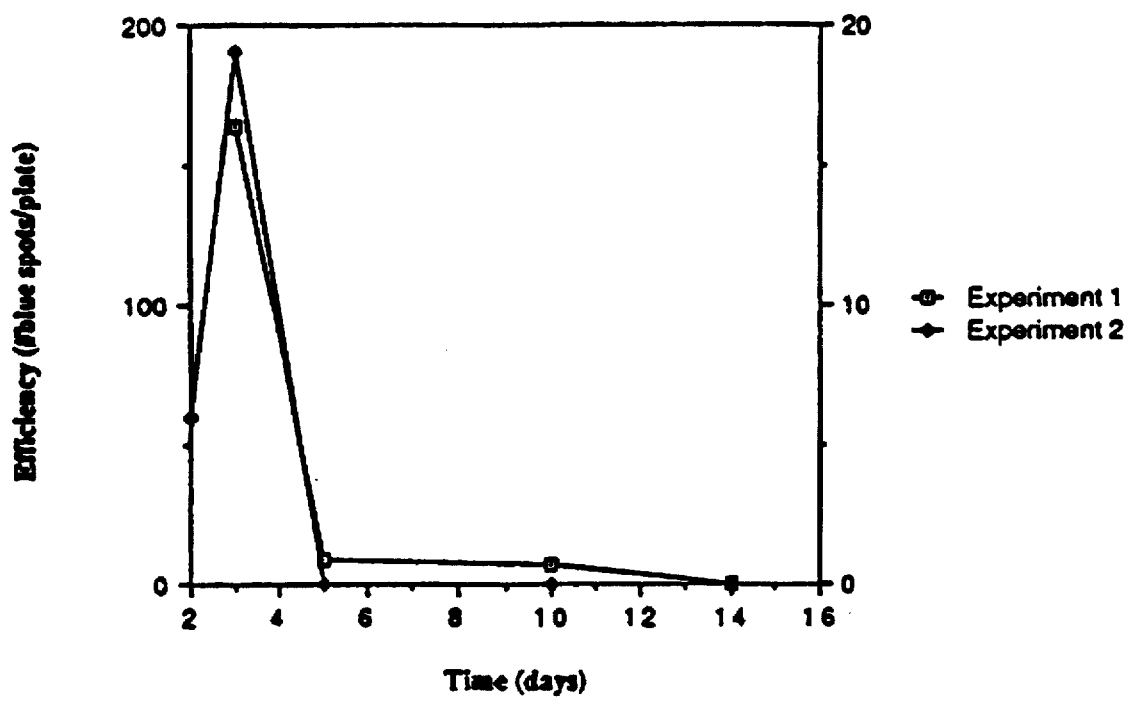
FIG. 8 shows expression of pHD203-GUS over time. Cells collected on filter paper by vacuum filtration were transferred onto NT1 medium solidified with 0.2% geirite and bombarded with helium entrainment configuration at 1500 psi, sample 8.1 cm from launch point using 1.0 sleeve level. At each time point (days after bombardment), cells were assayed for GUS activity. In both experiments, each treatment contained 3 replicates.

Cultured NT1 cells bombarded with either nuclear or chloroplast expression vectors were assayed for the expression of GUS upon the addition of a substrate mixture, three days after bombardment. Cells bombarded with either pUC118 or pBI101.3 (negative controls) showed no GUS activity. Cells bombarded with pBI505 (positive nuclear control) showed high levels of expression (the highest being roughly 15,000 transformants/plate) after overnight staining, and the blue color was distributed evenly throughout the whole cytosol of the stained cells. In contrast, cells bombarded with pHD203-GUS (chloroplast promoter) did not show GUS activity (blue spots) until after 4–5 days of staining. Enzyme activity (blue color) was primarily localized subcellularly. Chloroplast transient expression rates appeared to be 40–50 fold lower than nuclear transformation rates (the highest being 300–400 blue spots per petri plate). The expression of pHD203-GUS was maximal three days after bombardment and dropped rapidly (FIG. 8), which is consistent with our experience with CAT expression of repliconless chloroplast expression vectors (see above).

Confirmation of Organelle-Specific Expression of GUS

Figure 9:
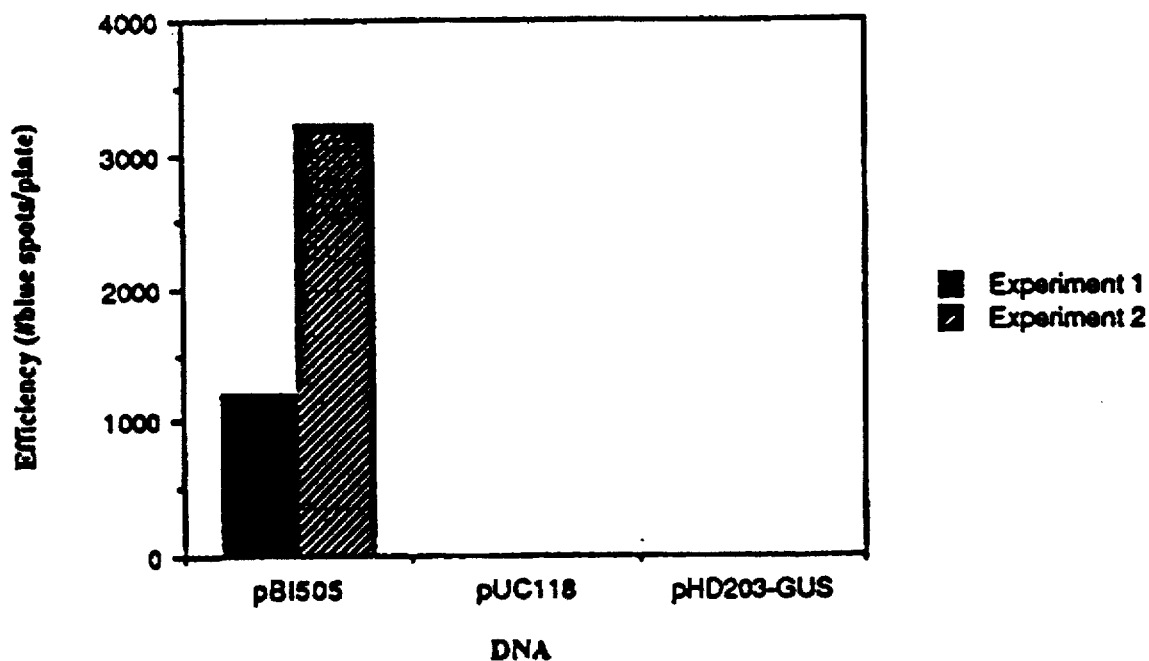
FIG. 9 shows transient expression of GUS activity following PEG-mediated protoplast transformation. In both experiments, each treatment contained 3 replicates.

To confirm that pHD203-GUS was truly expressing in the chloroplast, we needed to verify that it did not express in the nucleus. Therefore, pUC118, pBI505 and pHD203-GUS were introduced into tobacco NT1 protoplasts by PEG mediated transformation, followed by a GUS assay (FIG. 9). While pBI505 showed a high level of expression of GUS, no GUS activity was observed for either the negative control, pUC118, or the chloroplast expression vector, pHD203-GUS.

Optimization of Chloroplast Transformation

Figure 10:
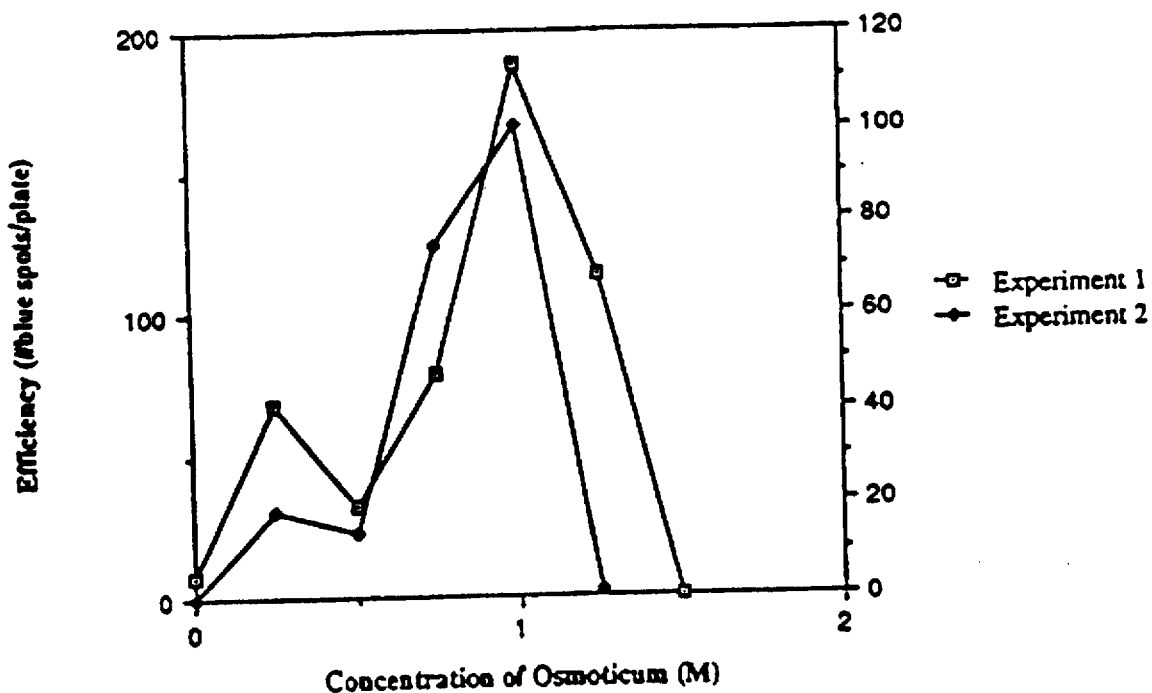
FIG. 10 shows effect of osmoticum on chloroplast transformation. NT1 cells collected on filter paper by vacuum filtration were transferred onto 0.2% geirite solidified NT1 media supplemented with different concentrations of osmoticum (½ sorbitol and ½ mannitol), incubated for at least 1.5 hour and bombarded. After three days of incubation, the cells were assayed for GUS activity. In experiment 1, each treatment had 5 replicates, and in experiment 2, each treatment had 4 replicates.

Osmoticum was found to have a major effect on transformation efficiency for both the chloroplast and the nucleus. When there was no supplemental osmoticum in the cell medium, chloroplast transformation was relatively low. As the concentration of osmoticum increased, transformation efficiency increased dramatically (about 20 fold) until it reached a maximum near 1.0M sorbitol/mannitol (FIG. 10). Further experiments confirmed that 1.1M sorbitol/mannitol was optimal for transient expression of GUS in chloroplasts of cultured NT1 cells. 1.5M osmoticum significantly reduced transformation efficiency. The importance of osmotic-support of bombarded cells has also been seen with yeast Armalco, et al., *Curr Genet* (1990) 17: 97–103. However, the optimal concentration of osmoticum for biolistic treatment varies greatly, ranging from 0.25M–1.75M, depending on the species.

The helium biolistic transformation device increased chloroplast transformation efficiency dramatically. The commonly used gun-powder and a new helium device were contrasted in parallel experiments. Chloroplast transformation efficiencies were less than one transformant per petri plate for the traditional gun powder charge driven device, with the best plate having eight transformants; in contrast, transformation efficiencies with the helium driven biolistic device were greater than 200 transformants per petri plate, with the best plates having 300–400 transformants.

Experiments were conducted comparing different launch configurations (flying disc vs. helium entrainment) at different pressures, sample levels and sleeve levels (Table 1 below). These tests were made without supplemental osmotic support in the media, so rates were not optimal. In general, the helium entrainment configuration yielded more transient transformants than the flying disc configuration with the same combinations of pressure, sample and sleeve levels. For the flying disc configuration, 900 psi pressure, 6.1 cm from target cells to particle launch point, and the highest sleeve level (0.55 cm from rupture disc to flying disc) yielded the best results (an average of 52 blue spots per plate). For the helium entrainment configuration, 1500 psi pressure, 8.1 cm from target to launch point and the middle sleeve level (1.0 cm from rupture disc to nylon mesh) were optimal (an average of 227 blue spots per plate).

TABLE 1

Effect of Configuration, Helium Pressure, Sample level And Sleeve Level in NT 1 Chloroplast Transformation Efficiency.

| Configuration | Pressure (Ph) | Sample Level[1] (cm) | Sleeve Level[2] (cm) | Efficiency[3] |
|---|---|---|---|---|
| Helium Entrainment | 900 | 6.1 | 1.6 | 174 |
| | | 6.1 | 0.55 | 134 |
| | | 8.1 | 1.0 | 124 |
| | 1200 | 8.1 | 1.6 | 163 |
| | | 4.1 | 1.6 | 60 |
| | | 8.1 | 0.55 | 36 |
| | | 6.1 | 1.0 | 9 |
| | 1500 | 6.1 | 1.6 | 59 |
| | | 6.1 | 0.55 | 46 |
| | | 4.1 | 1.0 | 2 |
| | | 8.1 | 1.0 | 227 |
| Flying Disc | 900 | 6.1 | 1.6 | 18 |
| | | 6.1 | 0.55 | 52 |
| | | 4.1 | 1.0 | 27 |
| | | 8.1 | 1.0 | 9 |
| | 1200 | 8.1 | 1.6 | 2 |
| | | 4.1 | 1.6 | 5 |
| | | 4.1 | 0.55 | 4 |
| | | 8.1 | 0.55 | 4 |
| | | 6.1 | 1.0 | 1 |
| | 1500 | 6.1 | 1.6 | 2 |
| | | 6.1 | 0.56 | 3 |
| | | 4.1 | 1.0 | 3 |
| | | 8.1 | 1.0 | 2 |

[1] cm distance from particle launch point to target cells.
[2] cm distance from rupture membrane to flying disc or nylon mesh.
[3] Efficiency was expressed as the number of blue spots per plate. Each treatment contained six replicates.

Example IV

Construction of Glyphosate Selection Vectors for Stable Chloroplast Transformation The non-selective, broad spectrum herbicide glyphosate, N-phosphonomethyl)-glycine, interferes with aromatic amino acid biosynthesis by inhibiting the shikimic acid pathway enzyme 5-enolpyruvyshikimic acid 3-phosphate (EPSP) synthase Steinrucker and Amrehin *Biochem. Biophys. Res. Commun.* (1980) 94: 1207–1212. Plant cell suspension cultures can adapt to increases in the glyphosate concentration in the growth medium by overproducing EPSP synthase. Gene amplification has been shown to be the basis of glyphosate tolerance in cultured *Petunia hybrida* cells Shah et al. *Science* (1986) 233: 478–481. However, a mutant-aroA gene from bacteria, that encodes EPSP synthase that is less sensitive to glyphosate has also been reported in *Salmonella typhimurium*. Comai et al. *Science* (1983) 221: 370–371.

A mutant EPSPS gene conferring a high level of resistance to glyphosate (pMON 894) from petunia is flanked at the 5' end by 35S promoter-enhancer elements and by T-DNA right border sequences at the 3' end. The EPSPS coding sequence (including the transit peptide sequence) was excised from pMON 894 as a BglII-SmaI fragment and was inserted into the MCS of pHD203 at BamHI-SmaI sites. Transit peptide (TP) sequences could not be deleted because of lack of proper restriction sites; however, this would not interfere with the function of EPSPS inside chloroplasts because TP would be naturally cleaved inside the plastids. The presence of TP did not interfere with EPSPS function in *E. coli* and was also found to be useful in distinguishing petunia EPSPS from endogenous EPSPS in *E. coli*.

In order to facilitate stable integration of EPSPS into the chloroplast genome, the 3' end of the psbA gene (rest of the coding sequence) will be inserted into the MCS present at the 3' end of EPSP coding sequence. This will facilitate integration of EPSPS directly into the psbA gene of the chloroplast genome. The distinct advantage of this border sequence would be that the EPSPS gene could be targeted into a known gene whose product is essential only for auxotrophic growth (psbA gene product, 32 kDa herbicide binding protein, functions in the photosynthetic electron transport chain). The disadvantage is that it will not be possible to regenerate green photosynthetic transgenic plants using this vector. However, this problem can be overcome by inserting an additional psbA coding sequence 5' to the left border sequence, as described later for atrazine selection. This would ensure that a new complete psbA gene is integrated into the ct genome, thereby enabling recovery of photosynthetic transgenic plants.

In order to increase the copy number of the introduced plasmid, a short pea chloroplast DNA fragment containing a replication origin (see above) identified as a displacement loop (D-loop), that has been tested by in vitro and in vivo DNA replication studies, will be inserted into appropriate restriction sites. This fragment will be inserted outside psbA border sequences in the chloroplast EPSPS vector so that it is used solely to amplify the copy number of the introduced plasmid and that it does not get integrated into the ct genome. Since this fragment is from the inverted repeat (IR) region (see above) it is unlikely that it would facilitate integration due to a copy correction mechanism operating between the inverted repeats (Blowers et al. *The Plant Cell* (1989) 1: 123–132.

Example V

Construction of Atrazine Selection Vectors

The chloroplast gene psbA codes for the photosynthetic quinone-binding membrane protein $Q_B$, which is the target of the herbicide atrazine. The mutant psbA gene from an atrazine resistant biotype of *Amaranthus hybridus* has recently been modified by fusing its coding region to transcription regulation and transit-peptide-encoding sequences for SSU of RuBisCO (Cheung et al. *Proc. Nat'l Acad. Sci (USA)* (1988) 85: 391–395. The mutant psbA gene will be excised from pSSU-S-ATR (obtained from Prof. Bogorad) as a BamH1 fragment that contains the entire mutant $Q_B$ protein encoding region and sequences coding for sixteen amino acids beyond the most probable initiation codon ATG of the $Q_B$ gene. This fragment will be made blunt (by filling in of the recessed 3' termini using Klenow fragment of *E. coli* DNA polymerase I) and inserted into the unique SmaI site present in the MCS, at the 3' end of the EPSPS coding sequence of pHD203-MK-EPSPS-TP (FIG. 1b). Plants transformed with this vector, though not selected on double herbicides, would still have both resistant genes stably integrated; a foreign gene unselected for, flanked by ctDNA sequences has been stably integrated and maintained in the chloroplast chromosome of Chlamydomonas. Cheung et al., supra.

From the above it can be seen that expression of exogenous DNA such as foreign genes or mutant mature genes inserted into the chloroplast genome may be obtained. The above results demonstrate that chloroplasts can be transformed efficiently and the exogenous genes expressed resulting in an altered chloroplast phenotype. As evidenced by the above disclosure, plant species having a modified genotype and phenotype and provided in which the chloroplast has been altered directly via its genome rather than indirectly by the use of modified proteins expressed via the nuclear genome and translocated into the chloroplast.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A DNA construct comprising:
    as operably joined components, at least one chloroplast replication origin functional in a plant chloroplast from other than a yeast, a transcriptional initiation region functional in a plant chloroplast, a heterologous DNA sequence encoding a polypeptide of interest, wherein transcription of said DNA sequence is regulated by said initiation region, and a transcriptional termination region.

2. The DNA construct according to claim 1, wherein said transcriptional initiation region is from a chloroplast gene.

3. The DNA construct according to claim 1, wherein said transcriptional initiation region is from a gene selected from the group consisting of a psbA gene, a rbcL gene and a atpB gene.

4. The DNA construct of claim 1 in which there is one chloroplast replication origin.

5. The DNA construct of claim 1 in which there are two chloroplast replication origins.

6. A chloroplast expression vector comprising:
    as operably joined components, at least one chloroplast replication origin functional in a plant chloroplast from other than a yeast, a transcriptional initiation region functional in a chloroplast, a DNA sequence comprising one or more cloning site(s) and a transcriptional termination region.

7. The expression vector according to claim 6, wherein said transcriptional initiation region is from a chloroplast gene.

8. The expression vector according to claim 6, wherein said transcriptional initiation region is from a gene selected from the group consisting of a psbA gene, a rbcL gene and a atpB gene.

9. The expression vector according to claim 6, wherein said cloning site is a multiple cloning site.

10. The expression vector according to claim 6, wherein said transcriptional termination region comprises at least one of a ribosomal RNA T1 terminator or a ribosomal RNA T2 terminator.

11. The expression vector according to claim 6, further comprising:

inserted into said cloning site in reading frame with said transcriptional initiation region, a heterologous DNA sequence encoding a polypeptide of interest.

12. The chloroplast expression vector of claim 6 in which there is one chloroplast replication origin.

13. The chloroplast expression vector of claim 6 in which there are two chloroplast replication origins.

14. A replication vector comprising:

as operably joined components, a DNA fragment comprising at least one chloroplast replication origin functional in a plant chloroplast from other than a yeast, a transcriptional initiation region functional in a plant chloroplast, a DNA sequence comprising one or more cloning site(s), and a transcriptional termination region.

15. A plant chloroplast comprising:

a DNA construct comprising, as operably joined components, at least one chloroplast replication origin functional in a plant chloroplast, a transcriptional initiation region functional in said chloroplast, a heterologous DNA sequence encoding a polypeptide of interest, wherein transcription of said DNA sequence is regulated by said initiation region, and a transcriptional termination region, wherein at least one of said components is heterologous to said chloroplast.

16. The plant chloroplast of claim 15 in which there is one chloroplast replication origin.

17. The plant chloroplast of claim 15 in which there are two chloroplast replication origins.

18. A plant chloroplast comprising:

a chloroplast expression vector comprising, as operably joined components, (1) a DNA fragment comprising at least one chloroplast replication origin functional in a plant chloroplast from other than a yeast, (2) a transcriptional initiation region functional in said chloroplast, (3) a DNA sequence encoding, a polypeptide of interest, and (4) a transcriptional termination region, wherein at least one of said components is heterologous to said chloroplast.

19. A plant chloroplast according to claim 18, wherein said plant is a higher plant.

20. A plant chloroplast containing heterologous DNA, wherein said chloroplast is obtained by the method of bombarding a plant cell with a DNA construct comprising an expression vector according to claim 11, wherein said DNA construct is adsorbed to a microprojectile.

21. A plant cell comprising:

a chloroplast according to claim 15 or claim 18.

22. The plant cell according to claim 21, wherein said plant cell is monocotyledonous or dicotyledonous.

23. The plant cell according to claim 21, wherein said cell is a wheat cell.

24. A method for introducing heterologous DNA into a chloroplast, said method comprising:

bombarding a plant cell with a chloroplast expression vector adsorbed to a microprojectile, said chloroplast expression vector comprising, as operably joined components, (1) at least one chloroplast replication origin functional in a plant chloroplast from other than a yeast, (2) a transcriptional initiation region functional in said plant chloroplast, (3) a heterologous DNA sequence encoding a polypeptide of interest, and (4) a transcriptional termination region whereby said heterologous DNA is introduced into chloroplast in said plant cell.

25. The method according to claim 24, wherein said plant cell is a higher plant cell.

26. The method of claim 24 for introducing heterologous DNA into a chloroplast in which there is one chloroplast replication origin.

27. The method of claim 24 for introducing heterologous DNA into a chloroplast in which there are two chloroplast replication origins.

28. A method for specifically modifying the phenotype of plant cell chloroplast distinct from other plant cell organelles, said the method comprising:

bombarding a plant cell with a chloroplast expression vector adsorbed to a microprojectile, said vector comprising, as operably joined components, (1) a DNA fragment comprising at least one chloroplast replication origin functional in a plant chloroplast from other than a yeast, (2) a transcriptional initiation region from a chloroplast gene, (3) a heterologous DNA sequence encoding a polypeptide of interest, and (4) a transcriptional termination region, wherein said components are functional in said chloroplast, and growing said plant cell whereby the phenotype of said plant chloroplast is modified as a result of expression of said DNA sequence.

29. The method according to claim 28, wherein said plant cell is in tissue selected from the group consisting of (1) leaf and (2) callus.

30. The method according to claim 28, wherein said plant cell is a wheat cell.

31. The method according to claim 28, wherein said microprojectile is delivered by a biolistic device selected from the group consisting of (1) a gun-powder driven device, (2) a flying disc device; and (3) a helium driven device.

32. The method according to claim 28, wherein prior to said introducing, said plant cell is incubated in medium containing osmoticum in an amount sufficient to increase transformation efficiency.

33. The method of claim 28 for specifically modifying the phenotype of a plant cell chloroplast in which there is one chloroplast replication origin.

34. The method of claim 28 for specifically modifying the phenotype of a plant cell chloroplast in which there are two chloroplast replication origins.

35. A method for specifically modifying the genotype of plant cell chloroplast distinct from other plant cell organelles, said method comprising:

bombarding a plant cell with a chloroplast expression vector absorbed to a microprojectile, said vector comprising, as operably joined components, (1) a DNA fragment comprising at least one chloroplast replication origin functional in a plant chloroplast, (2) a transcriptional initiation region from a chloroplast gene, (3) a DNA sequence encoding a polypeptide of interest, and (4) a transcriptional termination region, wherein said components are functional in said chloroplast and at least one of said components is heterologous to said plant cell, whereby a plurality of chloroplast in said plant cell are transformed and the genotype of said chloroplast is modified as a result of said introducing of said chloroplast expression vector.

36. The method of claim 35 for specifically modifying genotype of plant cell chloroplast in which there is one chloroplast replication origin.

37. The method of claim 35 for specifically modifying genotype of plant cell chloroplast in which there is one chloroplast in which there are two chloroplast replication origins.

* * * * *